(12) United States Patent
Habib

(10) Patent No.: US 8,293,726 B2
(45) Date of Patent: Oct. 23, 2012

(54) TREATMENT OF CANCER AND OTHER DISEASES

(75) Inventor: Nabil Francois Habib, Beirut (LB)

(73) Assignee: Vianova Labs, Inc., Cambridge, MA (US)

( * ) Notice: Subject to any disclaimer, the term of this patent is extended or adjusted under 35 U.S.C. 154(b) by 420 days.

(21) Appl. No.: 12/085,892

(22) PCT Filed: Nov. 30, 2006

(86) PCT No.: PCT/US2006/045665
§ 371 (c)(1),
(2), (4) Date: Mar. 6, 2009

(87) PCT Pub. No.: WO2007/064691
PCT Pub. Date: Jun. 7, 2007

(65) Prior Publication Data
US 2009/0226431 A1    Sep. 10, 2009

Related U.S. Application Data

(60) Provisional application No. 60/741,725, filed on Dec. 2, 2005.

(51) Int. Cl.
*A61K 31/56* (2006.01)

(52) U.S. Cl. .............. 514/182; 424/133.1; 514/171; 552/551

(58) Field of Classification Search .......... 514/171, 514/182; 552/551
See application file for complete search history.

(56) References Cited

U.S. PATENT DOCUMENTS 3,640,848 A    2/1972 Eyssen

FOREIGN PATENT DOCUMENTS

EP    0509656    10/1992
FR    7466 M * 1/1970

OTHER PUBLICATIONS

Cecil reference (Textbook of Medicine, 21st Edition (2000), Goldman & Bennett (Editors), WB, Saunders Company (Publisher), Chapter 198, pp. 1060-1074.*
Sausville et al, "Contributions of human tumor xenografts to anti-cancer drug development", Cancer Res. 2006, vol. 66 No. 7, Apr. 2006.*
Johnson et al "Relationships between drug activity in NCI preclinical in vitro and in vivo models and early clinical trials", British journal of Cancer, 2001, vol. 84, No. 10, pp. 1421-1431.*
Lens (Br. J. Nurs., 2008, vol. 17, No. 5, pp. 300-305).*
Divers et al (Cutis. 2004, vol. 73, No. 4, pp. 257-262.*
Chang et al "A cytotoxic butenolide, two dolebellane Diterpenoids, a Chroman and a Benzoquinol Derivatives Formosan Casearia membranacea", Planta Med 2003: vol. 69 pp. 667-672.*
Henri-STN Accession #:1971:436500, as evidenced by FR7466.*
Wang et al "New cytotoxic sulfated saponins from the starfish certonadoa semiregularis", Arch., Pharm., Res. vol. 28, No. 3, pp. 285-289, Mar. 2005.*
Pakrashi et al "Biological profile of the steroid stigmastane-3β,5α,6α-triol-monobenzoate", contraception, 1981, vol. 23, Issue 3, pp. 315-323.*
Mouse Fact web page accessed on Mar. 14, 2011.*
Choi et el., "Induction of Bax and activation of caspases during β-sitosterol-mediated apoptosis in human colon cancer cells," *International Journal of Oncology* 23:1657-1662 (2003).
Das et al., "Studies on marine chemicals, part VI. A new clionasterol derivative from the marine sponge *Spirastrella inconstans*," *Journal of Natural Products* 56:2210-2211 (1993).
Kovganko and Kashkan, "Synthesis of natural phytosteroids of the 6-ketostigmastane series and compounds related to them," *Chemistry of Natural Compounds* 26:656-660 (1990).
Minhas, "Current progress in lipid therapy," *The British Journal of Cardiology* 10:59-68 (2003).
Ong, "The statin studies: from targeting hypercholesterolaemia to targeting the high-risk patient," *QJM: Monthly Journal of the Association of Physicians* 98:599-614 (2005).
Park et al., "G2/M arrest of the cell cycle and apoptotic cell death by beta-sitosterol in human colon cancer cells," *FASEB Journal: Experimental Biology 2005 Meeting/35th International Congress of Physiological Sciences* Abstract 598.3 (2005).
Pascal et al., "Plant sterol biosynthesis," *Journal of Biological Chemistry* 268:11639-11654 (1993).
Zolotar' et al., "Structure-activity relationship for insecticidal steroids VI. 5,6-disubstituted β-sitosterols," *Chemistry of Natural Compounds* 38:167-170 (2002).
International Search Report (PCT/US06/45665), mailed Apr. 24, 2007.
Supplementary European Search Report (EP 06844623.6), dated Jun. 9, 2010.

* cited by examiner

*Primary Examiner* — Brandon Fetterolf
*Assistant Examiner* — Jean Cornet
(74) *Attorney, Agent, or Firm* — Clark & Elbing LLP

(57) ABSTRACT

The present invention relates to a novel compound (e.g., 24-ethyl-cholestane-3β,5α,6α-triol), its production, its use, and to methods of treating neoplasms and other tumors as well as other diseases including hypercholesterolemia, autoimmune diseases, viral diseases (e.g., hepatitis B, hepatitis C, or HIV), and diabetes.

29 Claims, 16 Drawing Sheets

TREATMENT OF CANCER AND OTHER DISEASES

CROSS-REFERENCE TO RELATED APPLICATIONS

This application is the national stage of International Application No. PCT/US2006/045665, filed Nov. 30, 2006, which, in turn, claims benefit of U.S. Application No. 60/741,725, filed Dec. 2, 2005.

BACKGROUND OF THE INVENTION

The invention relates to the treatment of neoplasms or other tumors as well as other diseases including hypercholesterolemia, autoimmune diseases, a viral diseases (e.g., hepatitis B, hepatitis C, or HIV), and diabetes.

Throughout the world there are public and government concerns about the increasing prevalence cancer. Many treatments exist but severe side effects and limited survival rate are pushing the research community into new approaches for treatments.

Cancer is a disease marked by the uncontrolled growth of abnormal cells. Cancer cells have overcome the barriers imposed on normal cells, which have a finite lifespan, to grow indefinitely. As the growth of cancer cells continue, genetic alterations may persist until the cancerous cell has manifested itself to pursue a more aggressive growth phenotype. If left untreated, metastasis, the spread of cancer cells to distant areas of the body by way of the lymph system or bloodstream, may ensue, destroying healthy tissue.

According to a recent American Cancer Society study, approximately 1,268,000 new cancer cases were expected to be diagnosed in the United States in the year 2001 alone. Lung cancer is the most common cancer-related cause of death among men and women, accounting for over 28% of all cancer-related deaths. It is the second most commonly occurring cancer among men and women; it has been estimated that there were more than 169,000 new cases of lung cancer in the U.S. in the year 2001, accounting for 13% of all new cancer diagnoses. While the rate of lung cancer cases is declining among men in the U.S., it continues to increase among women. According to the American Cancer Society, an estimated 157,400 Americans were expected to die due to lung cancer in 2001.

Cholesterol in Cell Membrane Activity

Cells require a flexible, permeable, fluid, active membrane. The cell membrane, which defines the cell and boundaries of cell organelles, is generally composed of lipid-cholesterol, phospholipids, sphingolipids, proteins, and carbohydrates. Cholesterol plays an important role in the flexibility, the fluidity, and the permeability of the membrane and the maintenance of these properties across a range of temperatures.

Cholesterol Synthesis and Uptake

Mammalian cells receive cholesterol through uptake of exogenic cholesterol and endogenous synthesis.

Exogenic uptake is mediated by specific receptors on the membrane itself; cholesterol is adsorbed from body fluids in contact with the cell. This uptake occurs through endocytosis of lipoprotein particles that contain cholesterol. The isomerization process of the phosphatidylcholine (FIG. 2) CC double bond cis/trans allow phospholipids with low density lipoprotein to contain specific receptors for cholesterol adsorption. Most animal cells acquire cholesterol by receptor-mediated endocytosis of low density lipoproteins that contain cholesterol to form endosomes which migrate to lysosomes for degradation and release of cholesterol into the cell.

By contrast, endogenous synthesis requires substantial energy. The synthesis of sterols (cholestane, vitamin D, and cholesterol) starts with squalene. Typically, cholesterol synthesis takes place in the cytoplasm of liver and intestinal cells through hydroxymethylglutaryl-CoA reductase (HMG-CoA reductase).

During the last three decades, cancer treatment was mainly focused on using cytotoxic products attacking both tumor and normal cells. There is therefore a need to finding additional targeted therapies to treat cancer with fewer side effects as compared to conventional therapies.

SUMMARY OF THE INVENTION

The invention features a substantially pure preparation of a compound described by the formula (I)

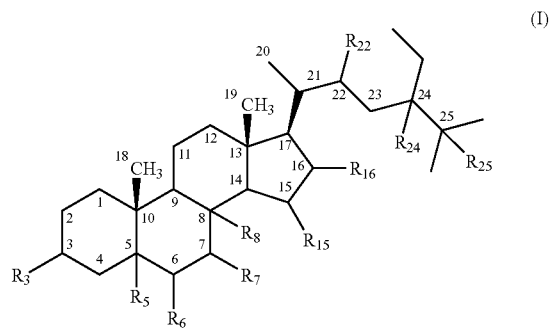

or a prodrug thereof.

In formula (I), each of $R_3$, $R_5$, and $R_6$ is, independently, selected from OH, SH, and $NH_2$; the stereochemistry at positions 3, 5, and 6 is either $3\alpha$, $5\beta$, $6\beta$ or $3\beta$, $5\alpha$, $6\alpha$; each of $R_7$, $R_8$, $R_{15}$, $R_{16}$, $R_{22}$, $R_{24}$, and $R_{25}$ is, independently, selected from H, OH, SH, and $NH_2$. In one embodiment, each of $R_3$, $R_5$, and $R_6$ is OH. An exemplary compound of formula (I) has the structure:

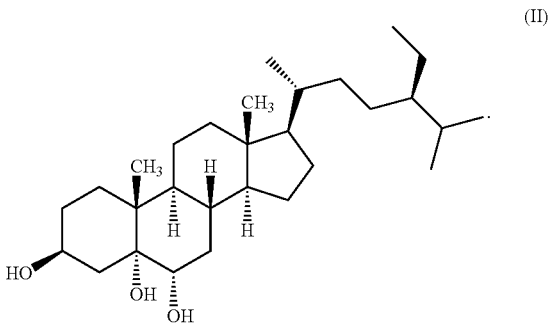

The compound can be part of a composition also including a pharmaceutically acceptable carrier and be suitable for oral, intravenous, topical, subcutaneous, buccal, intramuscular, inhalation, intrathecal, intraarticular, intratumoral, or rectal administration. When formulated for oral administration, the compound can be present, for example, in an amount between 0.005 mg and 500 mg, more desirably between 1 mg and 100 mg (e.g., 1, 5, 10, 20, 25, 30, 50, 75, or 100 mg).

The composition can further include another agent, such as an antiproliferative agent, an cholesterol-reducing agent, an antidiabetic agent, an antiinflammatory agent, or an antiviral agent. Exemplary agents are provided herein.

The invention also features a process for preparing 24-ethyl cholestane 3,5,6 triol comprising the step of oxidizing sitosterol. Using this process, for example, 24-ethyl cholestane 3β,5α,6α triol can be prepared from β-sitosterol, and 24-ethyl cholestane 3α,5β,6β triol can be prepared from α-sitosterol. There are many methods by which the sitosterol can be oxidized to prepare 24-ethyl cholestane 3,5,6 triol. In one such method, sitosterol is oxidized by reaction with periodate in the presence of osmium tetroxide.

If desirable, the compounds and compositions of the invention can be components of kits. Typically, a kit also includes instructions for administering the compound or composition for treating a disease (e.g., a neoplasm or other tumor).

The compounds, compositions, and kits of the invention can be employed in methods of treating diseases (e.g., any of the diseases provided herein). In particular, they can be employed in methods of treating cancer or other neoplasms. These compounds can also be used to treat hypercholesterolemia, autoimmune diseases, diabetes, and viral infections, among others. In a related aspect, the compounds and compositions of the invention can be used for the manufacture of a medicament for the treatment of any of the foregoing diseases.

The invention also features a method for treating a neoplasm comprising administering to a patient a compound or combination of compounds that inhibits HMG-CoA reductase and inhibits uptake of cholesterol into a cell.

Neoplasms that can be treated according to the invention include cancers such as leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), lung cancer (e.g., squamous cell carcinoma, adenocarinoma, or large cell carcinoma), colorectal cancer, ovarian cancer (e.g., ovarian adenocarcinoma), prostate cancer, polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma.

Autoimmune diseases that can be treated according to the invention include allergic bronchopulmonary aspergillosis; autoimmune hemolytic anemia; acanthosis nigricans; allergic contact dermatitis; Addison's disease; atopic dermatitis; alopecia greata; alopecia universalis; amyloidosis; anaphylactoid purpura; anaphylactical reaction; aplastic anemia; angioedema, hereditary; angioedema, idiopathic; ankylosing spondylitis; arteritis, cranial; arteritis, giant cell; arteritis, Takayasu's; arteritis, temporal; asthma; a-telangiectasia; autoimmune oophoritis; autoimmune orchitis; autoimmune polyendocrine failure; Behcet's disease; Berger's disease; Buerger's disease; bullous pemphigus; candidiasis, chronic mucocutaneous; Caplan's syndrome; post-myocardial infarction syndrome; post-pericardiotomy syndrome; carditis; celiac sprue; Chagas's disease; Chediak-Higashi syndrome; Churg-Strauss disease; Cogan's syndrome; cold agglutinin disease; CREST syndrome; Crohn's disease; cryoglobulinemia; cryptogenic fibrosing alveolitis; dermatitis herpetifomis; dermatomyositis; diabetes mellitus; Diamond-Blackfan syndrome; DiGeorge syndrome; discoid lupus erythematosus; eosinophilic fasciitis; episcleritis; drythema elevatum diutinum; erythema marginatum; erythema multiforme; erythema nodosum; familial Mediterranean fever; Felty's syndrome; fibrosis pulmonary; glomerulonephritis, anaphylactoid; glomerulonephritis, autoimmune; glomerulonephritis, post-streptococcal; glomerulonephritis, post-transplantation; glomerulopathy, membranous; Goodpasture's syndrome; graft-vs.-host disease; granulocytopenia, immune-mediated; granuloma annulare; granulomatosis, allergic; granulomatous myositis; Grave's disease; Hashimoto's thyroiditis; hemolytic disease of the newborn; hemochromatosis, idiopathic; Henoch-Schoenlein purpura; hepatitis, chronic active and chronic progressive; histiocytosis X; hypereosinophilic syndrome; idiopathic thrombocytopenic purpura; Job's syndrome; juvenile dermatomyositis; juvenile rheumatoid arthritis juvenile chronic arthritis); Kawasaki's disease; keratitis; keratoconjunctivitis sicca; Landry-Guillain-Barre-Strohl syndrome; leprosy, lepromatous; Loeffler's syndrome; Lyell's syndrome; Lyme disease; lymphomatoid granulomatosis; mastocytosis, systemic; mixed connective tissue disease; mononeuritis multiplex; Muckle-Wells syndrome; mucocutaneous lymph node syndrome; mucocutaneous lymph node syndrome; multicentric reticulohistiocytosis; multiple sclerosis; myasthenia gravis; mycosis fungoides; necrotizing vasculitis, systemic; nephrotic syndrome; overlap syndrome; panniculitis; paroxysmal cold hemoglobinuria; paroxysmal nocturnal hemoglobinuria; pemphigoid; pemphigus; pemphigus erythematosus; pemphigus foliaceus; pemphigus vulgaris; pigeon breeder's disease; pneumonitis, hypersensitivity; polyarteritis nodosa; polymyalgia rheumatica; polymyositis; polyneuritis, idiopathic; Portuguese familial polyneuropathies; pre-eclampsia/eclampsia; primary biliary cirrhosis; progressive systemic sclerosis (scleroderma); psoriasis; psoriatic arthritis; pulmonary alveolar proteinosis; pulmonary fibrosis, Raynaud's phenomenon/syndrome; Reidel's thyroiditis; Reiter's syndrome, relapsing polychrondritis; rheumatic fever; rheumatoid arthritis; sarcoidosis; scleritis; sclerosing cholangitis; serum sickness; Sezary syndrome; Sjogren's syndrome; Stevens-Johnson syndrome; Still's disease; subacute sclerosing panencephalitis; sympathetic ophthalmia; systemic lupus erythematosus; transplant rejection; ulcerative colitis; undifferentiated connective tissue disease; urticaria, chronic; urticaria, cold; uveitis; vitiligo; Weber-Christian disease; Wegener's granulomatosis; and Wiskott-Aldrich syndrome.

DEFINITIONS

By "prodrug" is meant any compound of the invention further modified in that one or more hydroxyl, sulfhydryl, or amino group of the compound is covalently attached to another molecule via a bond which is cleaved under in vivo conditions to form a free hydroxyl, free amino, or free sulfhydryl group, respectively. Thus, "prodrug" is intended to include any covalently bonded carrier that releases an active compound of the invention in vivo following administration to a subject. Prodrugs of the invention can be used, for example, with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1, pp. 172-178, 949-982 (1995). Examples of prodrugs that can be used include, without limitation, esters, thioesters, carbamates, and amides, among others.

By "substantially pure" is meant at least 10%, 20%, 30%, 40%, 50%, 60%, 70%, 80%, 90%, 95%, 98%, 99%, or greater purity of a compound. Additionally, "substantially pure" may refer to a compound of formula (I), where the compound is present in a composition in a ratio of at least 1.2, 1.5, 1.8, 2, 2.5, 3, 5, 10, or greater relative to related compounds with which it naturally occurs, without regard for other components of the composition. The naturally occurring compounds may include cholestane or cholestane derivatives, for example, isomers (e.g., stereoisomers) of a compound of formula (I).

By "antiproliferative agent" is meant any antiproliferative agent, including those antiproliferative agents listed in Table 1, any of which can be used in combination with a formula (I) compound to threat the medical conditions recited herein. Antiproliferative agents also include organo-platine derivatives, naphtoquinone and benzoquinone derivatives, chrysophanic acid and anthroquinone derivatives thereof.

TABLE 1

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |

TABLE 1-continued

| Category | | |
|---|---|---|
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | |
| | adenocarcinoma vaccine (Biomira) | ISF-154 (Tragen) |
| | CTP-37 (AVI BioPharma) | cancer vaccine (Intercell) |
| | IRX-2 (Immuno-Rx) | norelin (Biostar) |
| | PEP-005 (Peplin Biotech) | BLP-25 (Biomira) |
| | synchrovax vaccines (CTL Immuno) | MGV (Progenics) |
| | melanoma vaccine (CTL Immuno) | β-alethine (Dovetail) |
| | p21 RAS vaccine (GemVax) | CLL therapy (Vasogen) |
| Hormonal and antihormonal agents | estrogens | dexamethasone |
| | conjugated estrogens | prednisone |
| | ethinyl estradiol | methylprednisolone |
| | chlortrianisen | prednisolone |
| | idenestrol | aminoglutethimide |
| | hydroxyprogesterone caproate | leuprolide |
| | medroxyprogesterone | octreotide |
| | testosterone | mitotane |
| | testosterone propionate; | P-04 (Novogen) |
| | fluoxymesterone | 2-methoxyestradiol (EntreMed) |
| | methyltestosterone | arzoxifene (Eli Lilly) |
| | diethylstilbestrol | tamoxifen |
| | megestrol | toremofine |
| | bicalutamide | goserelin |
| | flutamide | Leuporelin |
| | nilutamide | bicalutamide |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |
| Kinase Inbibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |

TABLE 1-continued

| | |
|---|---|
| GW2016 (GlaxoSmithKline) | ABX-EGF (Abgenix) |
| EKB-509 (Wyeth) | IMC-1C11 (ImClone) |
| trastuzumab (Genentech) | Tyrphostins |
| OSI-774 (Tarceva ™) | Gefitinib (Iressa) |
| CI-1033 (Pfizer) | PTK787 (Novartis) |
| SU11248 (Pharmacia) | EMD 72000 (Merck) |
| RH3 (York Medical) | Emodin |
| Genistein | Radicinol |
| Radicinol | |

Miscellaneous agents

| | |
|---|---|
| SR-27897 (CCK A inhibitor, Sanofi-Synthelabo) | ceflatonin (apoptosis promotor, ChemGenex) |
| tocladesine (cyclic AMP agonist, Ribapharm) | BCX-1777 (PNP inhibitor, BioCryst) |
| alvocidib (CDK inhibitor, Aventis) | ranpirnase (ribonuclease stimulant, Alfacell) |
| CV-247 (COX-2 inhibitor, Ivy Medical) | galarubicin (RNA synthesis inhibitor, Dong-A) |
| P54 (COX-2 inhibitor, Phytopharm) | tirapazamine (reducing agent, SRI International) |
| CapCell ™ (CYP450 stimulant, Bavarian Nordic) | N-acetylcysteine (reducing agent, Zambon) |
| GCS-100 (gal3 antagonist, GlycoGenesys) | R-flurbiprofen (NF-kappaB inhibitor, Encore) |
| G17DT immunogen (gastrin inhibitor, Aphton) | 3CPA (NF-kappaB inhibitor, Active Biotech) |
| efaproxiral (oxygenator, Allos Therapeutics) | seocalcitol (vitamin D receptor agonist, Leo) |
| PI-88 (heparanase inhibitor, Progen) | 131-I-TM-601 (DNA antagonist, TransMolecular) |
| tesmilifene (histamine antagonist, YM BioSciences) | eflornithine (ODC inhibitor, ILEX Oncology) |
| histamine (histamine H2 receptor agonist, Maxim) | minodronic acid (osteoclast inhibitor, Yamanouchi) |
| tiazofurin (IMPDH inhibitor, Ribapharm) | indisulam (p53 stimulant, Eisai) |
| cilengitide (integrin antagonist, Merck KGaA) | aplidine (PPT inhibitor, PharmaMar) |
| SR-31747 (IL-1 antagonist, Sanofi-Synthelabo) | gemtuzumab (CD33 antibody, Wyeth Ayerst) |
| CCI-779 (mTOR kinase inhibitor, Wyeth) | PG2 (hematopoiesis enhancer, Pharmagenesis) |
| exisulind (PDE V inhibitor, Cell Pathways) | Immunol ™ (triclosan oral rinse, Endo) |
| CP-461 (PDE V inhibitor, Cell Pathways) | triacetyluridine (uridine prodrug, Wellstat) |
| AG-2037 (GART inhibitor, Pfizer) | SN-4071 (sarcoma agent, Signature BioScience) |
| WX-UK1 (plasminogen activator inhibitor, Wilex) | TransMID-107 ™ (immunotoxin, KS Biomedix) |
| PBI-1402 (PMN stimulant, ProMetic LifeSciences) | PCK-3145 (apoptosis promotor, Procyon) |
| bortezomib (proteasome inhibitor, Millennium) | doranidazole (apoptosis promotor, Pola) |
| SRL-172 (T cell stimulant, SR Pharma) | CHS-828 (cytotoxic agent, Leo) |
| TLK-286 (glutathione S transferase inhibitor, Telik) | trans-retinoic acid (differentiator, NIH) |
| | MX6 (apoptosis promotor, MAXIA) |
| PT-100 (growth factor agonist, Point Therapeutics) | apomine (apoptosis promotor, ILEX Oncology) |
| midostaurin (PKC inhibitor, Novartis) | urocidin (apoptosis promotor, Bioniche) |
| bryostatin-1 (PKC stimulant, GPC Biotech) | Ro-31-7453 (apoptosis promotor, La Roche) |
| CDA-II (apoptosis promotor, Everlife) | brostallicin (apoptosis promotor, Pharmacia) |
| SDX-101 (apoptosis promotor, Salmedix) | β-lapachone |
| rituximab (CD20 antibody, Genentech | gelonin |
| carmustine | cafestol |
| Mitoxantrone | kahweol |
| Bleomycin | caffeic acid |
| Absinthin | Tyrphostin AG |
| Chrysophanic acid | |
| Cesium oxides | |

By an "antihypercholesterolemia agent" is meant any drug that the lowers cholesterol level of a patient. An antihypercholesterolemia agent may function by reducing the synthesis of cholesterol in the patient. Antihypercholesterolemia agents include atorvastatin, cerivastatin, fluvastatin, lovastatin, pravastatin, rosuvastatin, simvastatin, colesevelam, cholestyramine, colestipol, nicotinic acid, gemfibrozil, probucol, and clofibrate By an "antiviral agent" is meant any compound that destroys a virus or that reduces a virus's ability to replicate or disseminate in vivo. Antiviral agents can be used therapeutically in combination with a formula (I) compound. Examples of antiviral agents include interferon-α, -β, -γ, ribavirin (1βD ribofuranosyl-1H-1,2,4 thiazole 3-carboxamide) and its derivatives, and the synthetic nucleotide analog lamivudine ((cis-1-[2'-Hydroxymethyl-5'-(1,3-oxathiolanyl)]cytosine) and its analogs. Other examples of antiviral agents include idoxuridine, vidarabine, trifluridine, acyclovir, famciclovir, penciclovir, valacyclovir, ganciclovir, foscarnet, amantadine, rimantadine, cidofovir, zidovudine, didanosine, zalcitabine, stavudine, nevirapine, delavirdine, saquinavir, ritonavir, indinavir, nelfinavir, adefovir dipivoxil, suramin, polycytidylic acid, 2',3'-dideoxy cytidine, or ubenimex. One skilled in the art would know how to assay the antiviral activity of an agent using an antiviral assay (e.g., the methods disclosed in e.g., Monkarsh et al., *Anal. Biochem.* 247:434-440, 1997; Grace et al., *J. Interferon Cytokine Res.* 21:1103-1115, 2001; Bailon et al., *Bioconj. Chem.* 12:195-202, 2001). Desirably, an "antiviral agent" results in a reduction in viral replication or dissemination of, for example, at least 10%, 20%, 30%, or 50%. In more desirable embodiments, an antiviral agent reduces viral replication or dissemination, for example, by at least 70%, 80%, 90%, 95%, or even 99%.

By "antidiabetic agent" is meant any compound that may be used to decrease at least one symptom of diabetes. Antidiabetic agents can be used in combination with formula (I) compounds for the treatment of diabetes. Exemplary antidiabetic agents include sulfonylureas, non-sulfonylurea secretagogues, insulin, insulin analogs, glucagon-like peptides, exendin-4 polypeptides, beta 3 adrenoceptor agonists, PPAR agonists, dipeptidyl peptidase Iv inhibitors, biguanides, alpha-glucosidase inhibitors, immunomodulators, statins and statin-containing combinations, angiotensin converting enzyme inhibitors, adenosine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin 1 antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists, insulin sensitizers, lipase inhibitors, melanin-concentrating hormone receptor antagonists, nerve growth factor agonists, neuropeptide γ agonists, neuropeptide Y antagonists, SNRIs, protein tyrosine phosphatase inhibitors, and serotonin 2C receptor agonists.

By "antiinflammatory agent" is meant any agent that reduces an inflammatory response. Antiinflammatory agents can be used in combination with formula (I) compounds for the treatment of autoimmune diseases and other inflammatory disorders. Exemplary agents include NSAIDs, COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators, DMARDs (e.g., methotrexate, leflunomide, minocycline, auranofin, gold sodium thiomalate, aurothioglucose, and azathioprine), and corticosteroids.

By "corticosteroid" is meant any naturally occurring or synthetic compound characterized by a hydrogenated cyclopentanoperhydrophenanthrene ring system and having immunosuppressive and/or antiinflammatory activity. Corticosteroids can be used in combination with formula (I) compounds for the treatment of autoimmune diseases and other inflammatory disorders. Naturally occurring corticosteroids are generally produced by the adrenal cortex Synthetic corticosteroids may be halogenated.

By "non-steroidal anti-inflammatory drug" or "NSAID" is meant any non-steroidal agent that decreases proinflammatory cytokine production or secretion, binds an immunophilin, or causes a down regulation of the proinflammatory reaction. NSAIDs can be used in combination with formula (I) compounds for the treatment of autoimmune diseases and other inflammatory disorders. NSAIDs include calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NSAIDs also include rapamycin (sirolimus) and everolimus, which bind to an FK506-binding protein, FKBP-12, and block antigen-induced proliferation of white blood cells and cytokine secretion.

By "small molecule immunomodulator" is meant a non-steroidal, non-NsIDI compound that decreases proinflammatory cytokine production or secretion, causes a down regulation of the proinflammatory reaction, or otherwise modulates the immune system in an immunophilin-independent manner. Small molecule immunomodulators can be used in combination with formula (I) compounds for the treatment of autoimmune diseases and other inflammatory disorders. Exemplary small molecule immunomodulators are p38 MAP kinase inhibitors such as VX 702 (Vertex Pharmaceuticals), SCIO 469 (Scios), doramapimod (Boehringer Ingelheim), RO 30201195 (Roche), and SCIO 323 (Scios), TACE inhibitors such as DPC 333 (Bristol Myers Squibb), ICE inhibitors such as pranalcasan (Vertex Pharmaceuticals), and IMPDH inhibitors such as mycophenolate (Roche) and merimepodib (Vertex Pharmaceuticals).

The terms "cancer" or "neoplasm" or "neoplastic cells" encompass neoplasms, cancers, or neoplastic cells located at the original site of proliferation ("primary tumor or cancer") and their invasion of other tissues, or organs beyond the primary site ("metastasis").

By "inhibits the growth of a neoplasm" is meant measurably slows, stops, or reverses the growth rate of the neoplasm or neoplastic cells in vitro or in vivo. Desirably, a slowing of the growth rate is by at least 20%, 30%, 50%, or even 70%, over a period of treatment of six month is achieved as determined using a suitable assay for determination of cell growth rates (e.g., a cell growth assay described herein). Typically, a reversal of growth rate is accomplished by initiating or accelerating necrotic or apoptotic mechanisms of cell death in the neoplastic cells, resulting in a shrinkage of the neoplasm.

By "an effective amount" is meant the amount of a compound or a combination of compounds required to treat or prevent a disease in a clinically relevant manner. An effective amount of a compound varies depending upon the disease being treated, the manner of administration, and the age, body weight, and general health of the patient Ultimately, the prescribers will decide the appropriate amount and dosage regimen according to good medical practice.

The term "administration" or "administering" refers to a method of giving a composition of the invention to a patient, by a route such as inhalation, ocular administration, nasal instillation, parenteral ministration, dermal administration, transdermal administration, buccal administration, rectal administration, sublingual administration, perilingual administration, nasal administration, topical administration and oral administration. Parenteral administration includes intrathecal, intraarticular, intratumoral, intravenous, intraperitoneal, subcutaneous, and intramuscular administration. The optimal method of administration of a drug or drug combination to treat a particular disease can vary depending on various factors, e.g., the oral bioavailability of the drug(s), the anatomical location of the disease tissue, and the severity of disease.

Other features and advantages of the invention will be apparent from the following Detailed Description, the drawings, and the claims.

DETAILED DESCRIPTION

Figure 1:
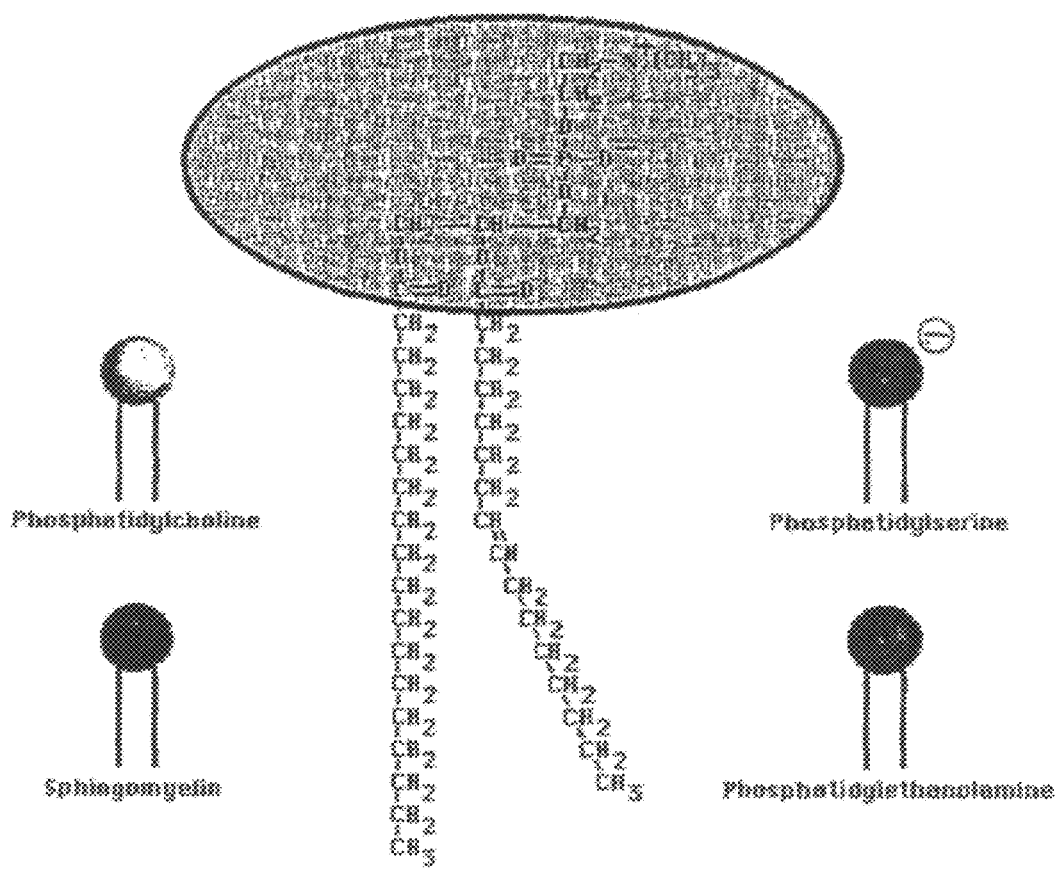
FIG. 1 is the structure of phosphatidylethanolamine.
Figure 2:
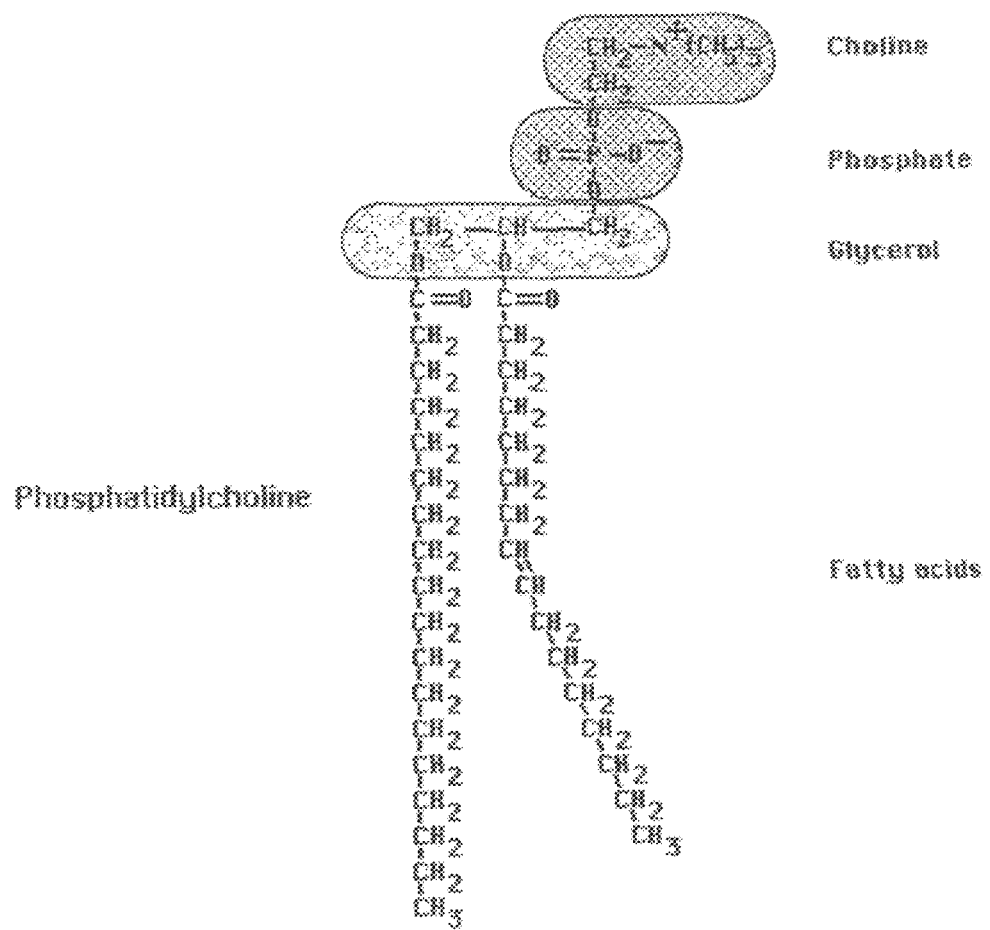
FIG. 2 is the structure of phosphatidylcholine.
Figure 3:
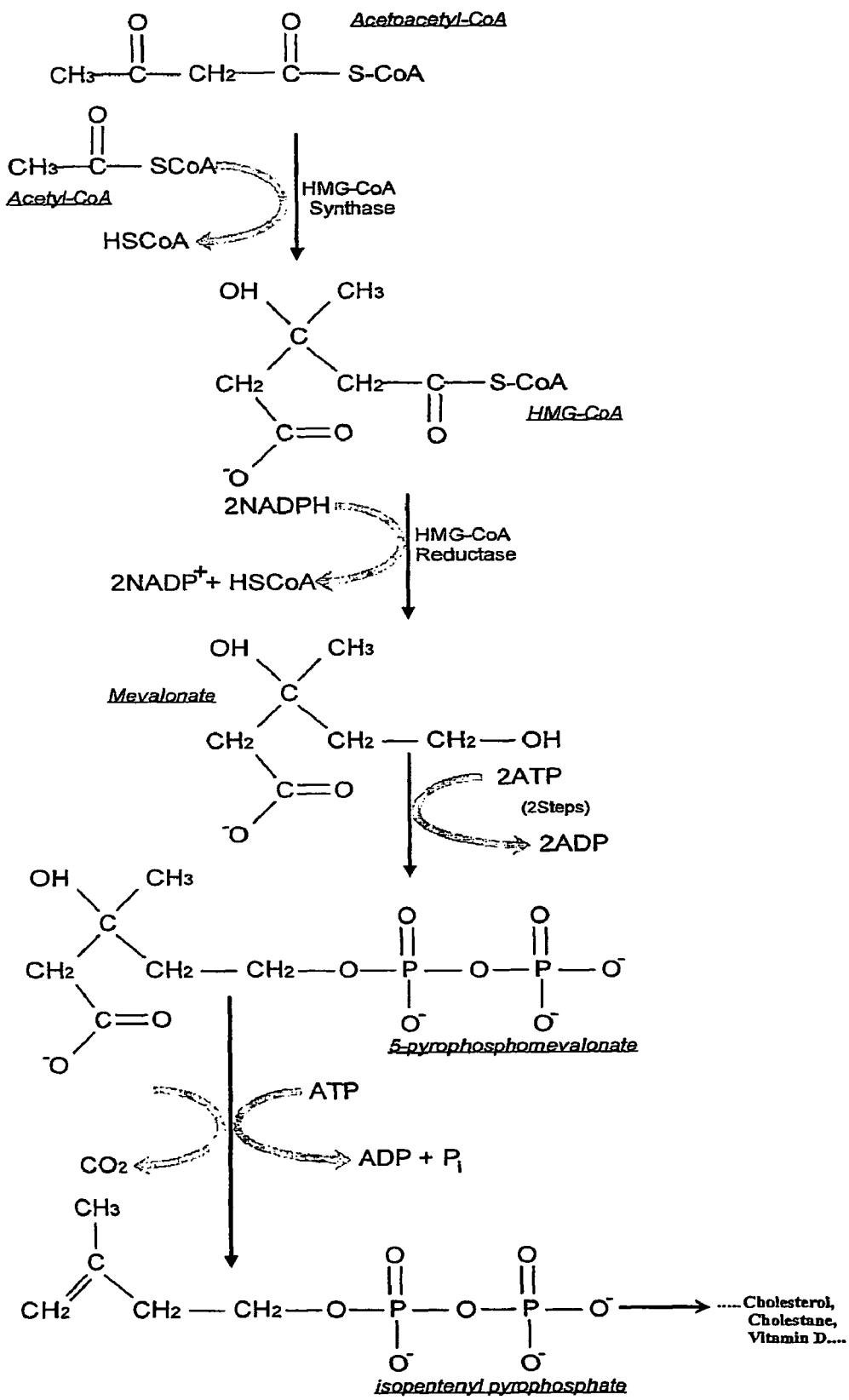
FIG. 3 is a schematic diagram showing the synthesis pathway of cholesterol.
Figure 4:
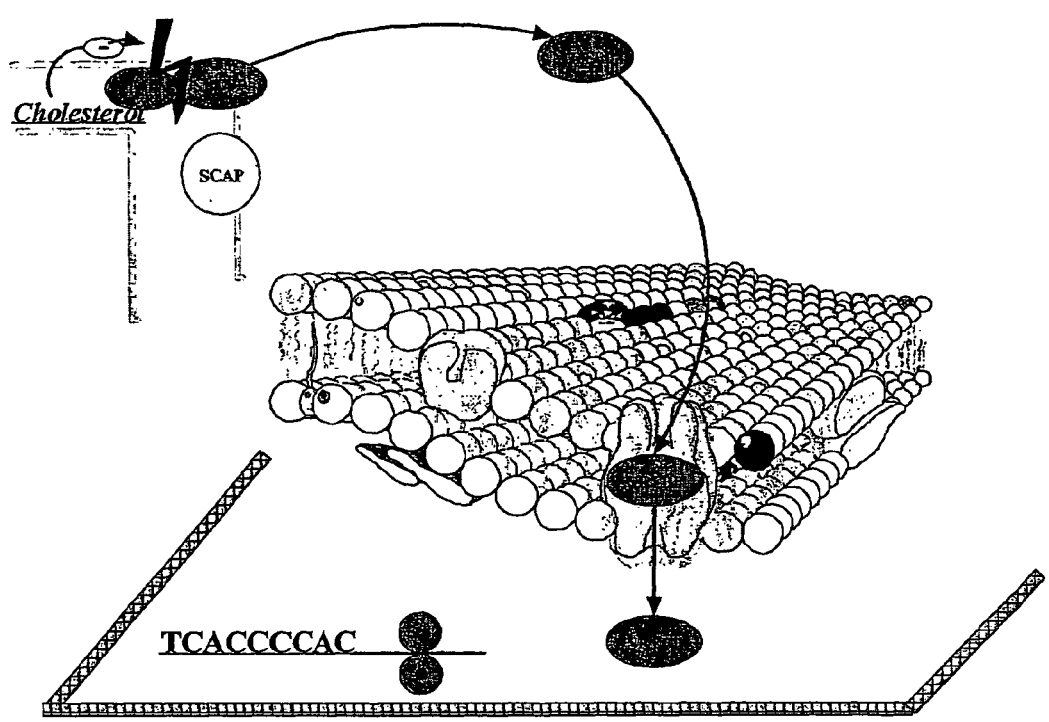
FIG. 4 is a schematic diagram showing the role of cholesterol and the sterol regulatory element binding protein (SREBP) in the regulation of cholesterol synthesis.

The invention features therapeutic uses of a compounds of formula (I) (e.g., 24-ethyl-cholestane-3β,5α,6α-triol)

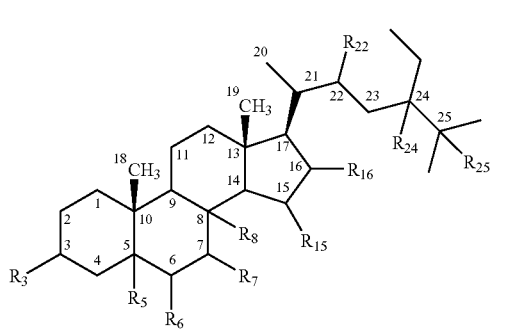

which, either alone or in combination with other therapies, may be used to treat neoplasms and other tumors. Diseases such as hypercholesterolemia, viral infections, autoimmune disorders, and diabetes may also be treated using a compound of formula (I). Accordingly, the present invention provides compositions that include a compound of formula (I), methods for synthesizing a compound of formula (I), uses of and methods of treatment using a compound of formula (I), and kits including compounds of formula (I).

Compositions

The invention provides compositions that include a compound of formula (I) or a prodrug (e.g, a prodrug described herein) of the compound.

Preparation of 24-ethyl-cholestane-3β,5α,6α-triol

A compound within formula (I), 24-ethyl-cholestane-3β,5α,6α-triol (formula (II)), shown below, may be synthesized using the following protocol.

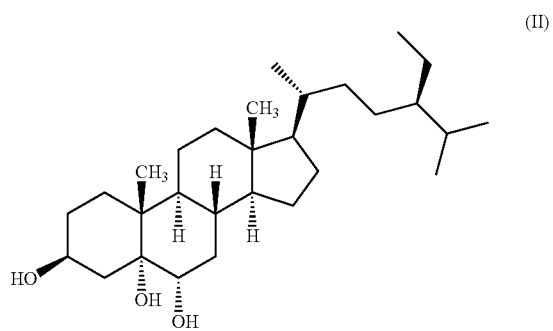

The starting material is betasitosterol (mp<140° C.) which as isolated is 60% (w/w) and which contains campesterol (mp>156° C.) and other sterols. The betasitosterol is diluted 15-fold in absolute ethanol (w/v) at 0° C. and allowed to separate into a liquid and solid phase. The liquid phase is discarded; the remaining solid phase is dissolved in the same volume of ethanol at 75° C.

Liquid and solid phases are again formed, and the solid residue is removed by filtration at 75° C. and discarded. The liquid phase is cooled to room temperature until the appearance of a solid residue.

This solid residue is heated to generate a liquid phase (160° C.). The material is very slowly and slightly cooled until a solid mass forms. The liquid phase is separated from the solid phase (which is discarded), cooled to room temperature, and added to pyridine at a ratio to 1/15 (w/v); 0.5 grams of osmium tetroxide and 2 times w/v $H_2O_2$ plus 0.1 grams $KIO_4$ are also added. The solution is stirred at room temperature for 12 hours and then heated under pyridine reflux for 3 hours. The solution is then cooled to 0° C., extracted with ether, and washed successively with a 5% HCl aqueous solution, water, an aqueous $Na_2CO_3$ solution, and water. The organic phase is then dried over $MgSO_4$ at low pressure.

The obtained solid is then dissolved in ethanol and heated until completely dissolved. Water is very slowly added until the appearance of a slight white precipitant, which is then filtered at the temperature of its formation. The solution is cooled, dissolved in acetone, and re-crystallized in acetone-water media, filtered and dried under $MgSO_4$ at low pressure.

Synthesis of Related Compounds

Compounds hydroxylated at positions other than 3, 5, and 6 can be prepared by enzymatic oxidation of sitosterol or phytosterols, for example, 24-ethyl-cholestane-3,5,6-triol, as shown below in Scheme 1.

Scheme 1

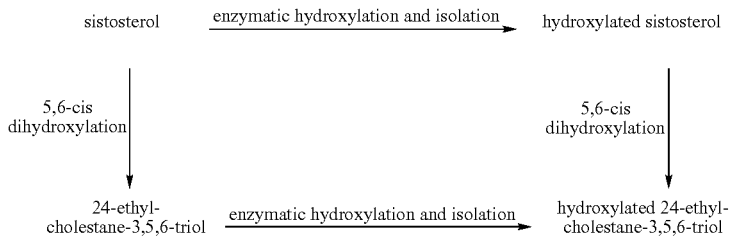

Enzymatic hydroxylations can be achieved, for example, by enzymatic oxidation using the P450 enzyme CYP3A4 (Research Diagnostics, Inc., product number RDI-CYP3A4). Either the commercially available enzyme can be used or the sitosterol or 24-ethyl-cholestane-3,5,6-triol can be incubated in liver microsomes or fermented in a microbial culture. See, for example, Ambrus et al., *Steroids* 60:621 (1995); Aringer L., *J. Biol. Chem.* 257:13720 (1982); Mahato et al., *Biochem. J.* 196:629 (1981); Aringer et al., *J. Lipid Res.* 17:263 (1976); and Aringer et al., *J. Lipid Res.* 14:563 (1973).

The reaction of an olefin with osmium tetroxide, described above, is the most reliable method for cis-dihydroxylation of a double bond, particularly for preparation of cis-diols. Cis-dihydroxylation of olefins may also be achieved using permanganate or silver iodoacetate according to Woodward's procedure. A variety of synthetic conditions and oxidizing agents are known to be capable of cis-hydroxylation of an olefin and may be used in the synthesis of the compounds of the invention. See, for example, VanRheenen et al., *Organic Syntheses, Coll.* 6:342 (1988); Vol. 58, p. 43 (1978).

Protection and Deprotection of Reactive Groups

The synthesis of compounds of the invention may include selective protection and deprotection of alcohols, amines, and/or sulfhydryls functional groups. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. An acetal can be used to protect the 5-hydroxy and 6-hydroxy positions of an intermediate or compound of the invention Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, and sulfhydryl functionalities and the conditions required for their removal are provided in detail in "T. W. Green and P. G. M. Wuts: Protective Groups in Organic Synthesis" ($2^{nd}$ ed., 1991, John Wiley & Sons) and "P. J. Kocienski: Protecting Groups" (1994 Georg Thieme Verlag); each of which is hereby incorporated by reference.

Synthesis of Sulfhydryl and Amine Derivatives

An unprotected hydroxyl in a compound of the invention can be activated using standard techniques (e.g., conversion to a tosylate, brosylate, mesylate, triflate or other reactive leaving group see, for example, J. March, Advanced Organic Chemistry: Reactions, Mechanisms and Structure, John Wiley & Sons, Inc. pp. 352-354, 1992). The conversion of the activated alcohol to a sulfhydryl group can be achieved by either addition of sulfide (e.g., NASH, $Na_2S$), addition of disulfide (e.g., $Na_2S_2$) followed by reduction of the disulfide to a sulfhydryl group, or transesterification of the activated alcohol with thioacetate followed by hydrolysis to the sulfhydryl with sodium acetate. The conversion of the activated alcohol to an amino group can be achieved by either addition of an amine or addition of azide followed by reduction to the amino group.

Formulation of Pharmaceutical Compositions

The compositions including a compound of formula (I) are formulated such that an effective amount of compound reaches the target region (e.g., a neoplasm). The compound may be contained in any appropriate amount in any suitable carrier substance, and is generally present in an amount of 1-95% by weight of the total weight of the composition. The composition may be provided in a dosage form that is suitable for oral, parenteral (e.g., intrathecally, intraarticularly, intratumorally, intravenously, intramuscularly), rectal, cutaneous, nasal, vaginal, inhalant, skin (patch), or ocular administration route.

Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy*, 20th edition, 2000, ed. A R Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

For compositions that include combinations of compounds, each compound of the combination may be formulated in any variety of ways that are known in the art. For example, the first and second agents may be formulated together or separately. Desirably, the first and second agents are formulated together for the simultaneous or near simultaneous administration of the agents. Such co-formulated compositions can include the compound of formula (I) and, for example, an antiproliferative agent formulated together in the same pill, capsule, liquid, etc.

The individually or separately formulated agents can be packaged together as in a kit. Non limiting examples include kits that contain, e.g., two pills, a pill and a powder, a suppository and a liquid in a vial, two topical creams, among others. The kit can include optional components that aid in the administration of the unit dose to patients, such as vials for reconstituting powder forms, syringes for injection, customized IV delivery systems, inhalers, among others. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Dosages

Dosages of a compound of the invention may range from 0.005 mg/kg to 2000 mg/kg body weight per day (mg/kg/day). For example, a dose of 0.01, 0.05, 0.1, 0.2, 0.25, 0.3, 0.4, 0.5, 0.75, 1.0, 1.25, 1.5, 1.75, 2.0, 2.5, 3, 4, 5, 8, 10, 25, 50, 100, 250, 500, 750, 1000, 1250, 1500, or 1750 mg/kg/day may be provided to the patient. Typically, a patient suffering from a neoplasm is given 1 mg/kg/day initially. Once a 50% remission of the neoplasm is achieved, the dosage may be reduced to 0.5 mg/kg/day. Further six months following the 50% remission, the dose may be further decreased to 0.25 mg/kg/day. This treatment may be continued indefinitely, or may be discontinued if it appears the neoplasm has been successfully treated. If a patient does not achieve a 50% remission, or is at an advanced stage of disease, the initial dose may be doubled to 2 mg/kg/day until 50% remission is achieved. Dosages are typically given orally. In one embodiment, capsules each contain 10 mg of the compound. To achieve a 1 mg/kg/day dosing, a 60 kg individual may take 6 capsules each containing 10 mg of the compound each day, where one capsule is taken at time intervals spaced throughout the day.

The dosage of each compound or agent of the claimed compositions may additionally depend on other factors, including: the administration method, the disease (e.g., a neoplasm or other tumor, hypercholesterolemia, a viral infection, an autoimmune disease) to be treated, the severity of the disease, whether the disease is to be treated or prevented, site of the diseased tissue (e.g., a tumor), and the race, gender, age, weight, and health of the patient to be treated. Ultimately dosing will be determined by a physician or other prescriber of treatment based on these factors. Dosages may be altered (e.g., lowered) where a compound of the invention is administered in combination with a second therapeutic. For example, in the case of treating a patient with a neoplasm or other tumor, a lower dose of a compound of the invention may be provided when given in conjunction with a chemotherapeutic agent (e.g., an antiproliferative described herein).

Therapy

Compounds of formula (I) and compositions including compounds of formula (I) are administered to a patient for the treatment of a neoplasm such as cancer. Other diseases that may be treated by the methods of the invention include hypercholesterolemia, a viral infection such as hepatitis (e.g., hepatitis A, hepatitis B, hepatitis C, hepatitis D, or hepatitis E) or HIV, an autoimmune disorder (e.g., psoriasis or other diseases described herein), and diabetes, in particular, type II diabetes.

Any composition or formulation including a compound of formula (I) and any mode of delivery may be used to provide treat the patient including oral, intrathecal, intraarticular, intratumoral, parenteral (e.g., intravenously, intramuscularly), rectal, cutaneous, nasal, vaginal, inhalant, skin (patch), or ocular administration. Therapeutic compositions may be administered to patients who exhibit at least one symptom of a disease, to prevent the development of disease, or to maintain a reduction of disease achieved by administration of a compound of the invention or another therapy.

Compounds of formula (I) or compositions comprising a compound of formula (I) and another therapeutic or therapeutics may be administered together. For example, treatment of a neoplasm, an autoimmune disorder, or a viral infection may include administration of a compound of formula (I) together with an antiproliferative agent, an antiinflammatory agent, or an antiviral agent respectively. The combination administered may include one or more compounds in a subtherapeutically effective amount as determined separately for each compound.

In one example, a compound of formula (I) with an additional therapeutic agent are administered to a patient. After symptoms of the disease have decreased, administration of the additional agent is discontinued. The administration of a compound of formula (I) is then used to maintain the improved state of the patient following successful treatment with the combination of therapies. Such an approach may be particularly advantageous in cases where the additional agent has undesired side effects.

Neoplasms and Other Tumors

A formula (I) compound may be administered to treat a patient who has, or has an increased propensity to develop, a cancer or other neoplasm. Administration of the compound may be performed alone or in combination with existing therapies for neoplasms, such as chemotherapy, radiation therapy, surgery, or a personalized vaccine.

Chemotherapy employs chemical agents to treat neoplasms. Exemplary chemotherapeutic (e.g., antiproliferative) agents are shown in Table 1. As with radiation therapy, chemotherapy typically targets rapidly dividing cells, which include neoplastic cells.

Radiation therapy uses isotopes (e.g., cesium ($^{137}$Cs) cobalt ($^{60}$Co) iodine ($^{131}$I), phosphorus ($^{32}$P) gold ($^{98}$Au) iridium ($^{192}$Ir) yttrium ($^{90}$Y, or palladium ($^{103}$Pd)) to treat cancer. The radioactivity selectively kills rapidly dividing cells that include neoplastic cells. Methods of administration include brachytherapy such as seed implants, where a radioactive substance in implanted in the body at or near the location of the neoplasm, radioactivity from external sources such as external beam radiation therapy.

A common approach used to treat cancer is surgery. Once a tumor has been identified, a surgeon can physically remove the tumor or a portion thereof from the patient.

Personalized vaccines employ antibodies directed toward a tumor found in the individual cancer patient. Such vaccines may be prepared as described in Hockertz, *Toxicology.* 214: 151-161, 2005 and Morse et al., *Nat Clin Pract Oncol.* 2005 2:108-113, 2005 and references cited therein. To prepare such a vaccine, a sample containing either all or part of the tumor is removed from the patient using surgical techniques, and cells or proteins are isolated from the tumor. Isolated proteins are preferably expressed preferentially in tumor cells as compared to normal cells. These cells or proteins, in conjunction with an adjuvant that increases immune reactivity, are injected into the patient. This induces an immune response to the injected cells or proteins, a response which is targeted to the tumor composed of these cells or targeted to tumor cells that contain these proteins.

Hypercholesterolemia

A formula (I) compound may also be administered to a patient suffering from hypercholesterolemia. The compound can block synthesis of cholesterol through HMG-CoA reductase inhibition, thereby reducing cholesterol levels, thus decreasing the risk of diseases including arteriosclerosis, heart disease, and heart attacks. Formula (I) compounds may be combined with other antihypercholesterolemia agents.

Viral Infections

Administration of a formula (I) compound has been shown to be effective in treating a patient having a viral infection such as HIV, hepatitis B, and hepatitis C. As the mechanism of action appears to be inhibition of reverse transcription, a formula (I) compound the invention may be useful for treating many retroviral infections. Formula (I) compounds may be combined with other antivirals.

Autoimmune Disorders

A formula (I) compound may be administered to a patient suffering from an autoimmune disorder such as psoriasis, rheumatoid arthritis, or any other such disease listed herein. Administration of a compound of the invention may be further include administration of an antiinflammatory agent, such as those described herein.

Diabetes

A formula (I) compound may be administered to a patient suffering from diabetes. This administration may further include administration of an antidiabetic compound, such as those described herein.

Mode of Action—Antineoplastic Activity

I believe that formula (I) compounds both inhibit the activity of HMG-CoA reducatase, and competitively bind receptors involved in exogenous cholesterol adsorption. Inhibition of HMG-CoA reductase occurs in both normal cells and neoplastic cells; however, neoplastic cells are additionally rendered unable to adsorb exogenous cholesterol following administration of a formula (I) compound. This selectivity for neoplastic cells occurs for two reasons. First, tumors are poorly vascularized, which leads to a reduced supply of available exogenous cholesterol. Second, the reduced vascularization additionally leads to hypoxia, thereby increasing the concentration of anaerobic metabolic products, including lactic acid, pyruvic acid and carbon dioxide. Further, poor vascularization decreases the rate of carbon dioxide removal from the tumor tissue. Increased levels of carbon dioxide, in turn, leads to increased levels of carbonic acid, the formation of which is catalyzed by carbonic anhydrase. These factors reduce the pH of the environment surrounding the cells from a pH of 7.3-7.4 found in normal cells to pH 6.4-6.8.

The lower pH environment in neoplastic cells causes the administered formula (I) compound, e.g., 24-ethyl-cholestane-3β,5α,6α-triol, to migrate towards intercellular interstitial acidic fluid, and also increases the affinity of 24-ethyl-cholestane-3β,5α,6α-triol for the cholesterol receptors. This increased affinity, in combination with the reduced cholesterol concentration present in the fluid surrounding tumor cells, leads to specific, irreversible binding of the compound to the receptor. In the case of 24-ethyl-cholestane-3β,5α,6α-triol, binding is mediated by the three highly hydrophilic hydroxyl groups interacting with carbonyl groups of the receptor. The positions 3β, 5α, 6α hydroxides further provoke distortion of the membrane layers, and the ethyl group at position 24 plays the role of a "check valve," fixing the hydrophobic tail between the two lipidic layers.

In addition to binding the receptors directly, 24-ethyl-cholestane-3β,5α,6α-triol alters the three-dimensional structure of remaining unbound cholesterol receptors through distortion of the lipid bilayer. This alteration is sufficient to prevent adsorption of cholesterol molecules. The distortion of the lipid bilayer has other effects as well. The permeability and the fluidity of the bilayer membrane is also reduced, thus decreasing passive, mediated, and active diffusion across the membrane. This alteration can further decrease nutrition level of tumor cells.

Feedback Down-Regulation of Cholesterol Synthesis in Tumor Cells

Sterol feedback control, mediated by sterol regulatory element binding proteins (SREBPs) exerts the primary regulation on HMG-CoA reductase activity at the transcriptional level. Secondary regulation and non sterol isoprenoid-mediated fine tuning of reductase activity occurs at the levels of reductase translation and degradation. Reductase activity in tumors is elevated and resistant to sterol feedback regulation to aberrant SREBPs activity. Tumor reductase remains sensitive to 24-ethyl-cholestane-3β,5α,6α-triol post-transcriptional down-regulation.

Treating a Neoplasm by Inhibition of HMG-coA Reductase and Specific Inhibition of Cholesterol Uptake into Neoplastic Cells.

The invention also provides a method of treating a neoplasm by administering to a patient a compound or combination of compounds that inhibits HMG-CoA reductase and prevents uptake of cholesterol into neoplastic cells. Compounds that inhibit HMG-CoA reductase are known in the art and include atorvastatin, cerivastatin, fluvastatin, lovastatin, pravastatin, and simvastatin. An exemplary compound that inhibits cholesterol uptake is 7-ketocholesterol.

The following examples are intended to illustrate, rather than limit, the invention.

EXAMPLES

Example 1

Assessment of the Therapeutic Efficacy of 24-ethyl-cholestane-3β,5α,6α-triol in Mice Having Experimentally Induced Large B-Cell Lymphoma Investigations were carried out on immunocompromised laboratory mice with experimentally-induced large B-cell lymphoma using hematological, immunological, biochemical, anatomical, and cytological methods. Two groups of 15 mice were employed. In the first group, 24-ethyl-cholestane-3β,5α,6α-triol was administered orally daily at a dosage of 5 mg/kg. The second group served as the control. The following parameters of therapeutic efficacy were compared: dynamics of LDH activity in the blood plasma, content of total protein, and general clinical blood test results. As a reference, the results in mice having experimentally induced large B-cell lymphoma and healthy mice are shown in Table 2

TABLE 2

| Parameter | Group of animals | | Student's coefficient (P) |
|---|---|---|---|
| | Lymphoma | Healthy | |
| Erythrocytes lOO 12/1 | 10.02 ± 1.27 | 10.65 + 0.99 | 0.22 |
| Leukocytes $10^9$/L | 12.9 + 2.06 | 9.34 + 0.66 | 0.0003 |
| Hematocrit, L/L | 0.34 ± 0.016 | 0.34 + 0.011 | 0.67 |
| Color | 1.21 ± 0.18 | 1.4 + 0.11 | 0.0038 |
| Hemoglobin g/L | 149.4 + 7.94 | 166.6 ± 7.45 | 0.0001 |
| Lymphocytes, $10^9$/L | 9.03 + 1.45 | 6.54 + 0.46 | 0.00032 |
| Total protein g/L | 52.9 ± 1.96 | 56.2 + 2.36 | 0.0019 |
| LDH, U/L | 1228.9 + 139.8 | 444.1 + 48.9 | 0.000000023 |

As is seen from Table 2, statistically important differences (P<0.05) between animals with lymphoma and healthy animals were marked by the amount of leukocytes, hemoglobin, by color indication, the absolute number of lymphocytes in blood, as well as the content of total protein in the blood serum and the LDH activity in blood plasma. These changes characterize the presence of disorders in the lymphoid component of blood formation, indicate the presence of intensive cytolysis in the process of carcinogenesis (due to increased LDH), and show the presence of processes suppressing biosynthesis of protein.

Figure 5:
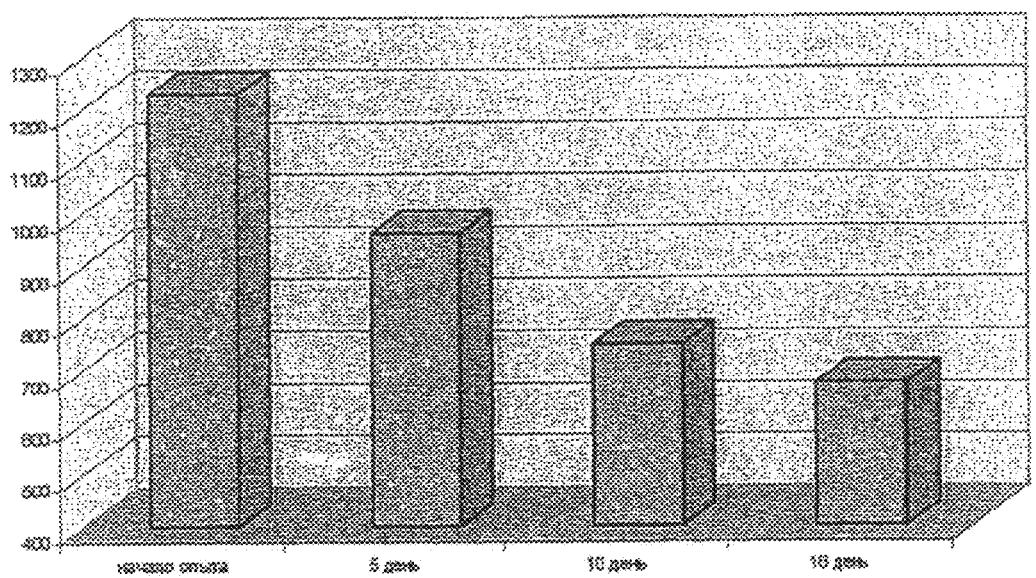
FIG. 5 is a graph showing a decrease in LDH activity in the blood plasma in diseased mice treated with a compound of formula (I).

The dynamics of therapeutic measures with the use of 24-ethyl-cholestane-3β,5α,6α-triol showed significant changes in chosen parameters (Table 3). The total content of protein in the blood serum and the hemoglobin concentration are increased. At the same time, a decrease in LDH activity in the blood plasma and in the number of lymphocytes was observed (FIG. 5). LDH activity in blood plasma in diseased mice treated with 24-ethyl-cholestane-3β,5α,6α-triol decreased 42.3% by the sixteenth day of treatment and, in some animals, LDH reached the level of healthy animals.

TABLE 3

BLOOD TEST RESULTS

| Animal group | Animal JVp | erythrocytes, 1012/1 | nieukocytes, 109/I | rhematocryte, I/I | thrombocytesl$O^9$/l |
|---|---|---|---|---|---|
| Healthy | 1 | 10.68 | 8.6 | 0.336 | 329 |
|  | 2 | 12.90 | 10.3 | 0.345 | 368 |
|  | 3 | 11.26 | 8.9 | 0.349 | 376 |
|  | 4 | 9.68 | 9.2 | 0.355 | 365 |
|  | 5 | 9.85 | 10.5 | 0.329 | 348 |
|  | 6 | 10.59 | 9.6 | 0.336 | 398 |
|  | 7 | 11.25 | 9.7 | 0.348 | 406 |
|  | 8 | 9.53 | 8.6 | 0.329 | 337 |
|  | 9 | 10.27 | 8.8 | 0.333 | 326 |
|  | 10 | 11.30 | 8.9 | 0.352 | 415 |
|  | 11 | 9.89 | 9.6 | 0.329 | 361 |
|  | M | 10.65 | 9.34 | 0.34 | 366 |
|  | m | 0.99 | 0.66 | 0.010 | 30.5 |
|  | P | 0.5079 | 0.4516 | 0.2035 | 0.3655 |
| Lymphoma | 1 | 110.32 | 14.8 | 0.339 | 289 |
|  | 2 | 9.58 | 12.6 | 0.356 | 386 |
|  | 3 | 8.96 | 9.3 | 0.327 | 361 |
|  | 4 | 11.28 | 11.9 | 0.338 | 326 |
|  | 5 | 10.53 | 12.8 | 0.328 | 298 |
|  | 6 | 8.53 | 16.5 | 0.346 | 295 |
|  | 7 | 12.02 | 12.9 | 0.345 | 302 |
|  | 8 | 11.25 | 10.7 | 0.338 | 329 |
|  | 9 | 9.52 | 12.9 | 0.337 | 338 |
|  | 10 | 8.23 | 14.6 | 0.329 | 359 |
|  | M | 10.02 | 12.90 | 0.34 | 328.30 |
|  | m | 1.27 | 2.06 | 0.01 | 32.84 |
|  | P | 0.22 | 0.00032 | 0.67 | 0.01 |
| Lymphoma 5th day of observation | 1 | 10.13 | 15.2 | 0.322 | 316 |
|  | 2 | 9.56 | 11.8 | 0.346 | 327 |
|  | 3 | 8.78 | 13.6 | 0.349 | 287 |
|  | M | 9.49 | 13.53 | 0.34 | 310.00 |
|  | m | 0.68 | 1.70 | 0.01 | 20.66 |
|  | P | 0.3748835 | 0.6198083 | 0.9439412 | 0.2951996 |
| Lymphoma 10th day of observation | 1 | 10.53 | 10.2 | 0.316 | 389 |
|  | 2 | 9.16 | 13.9 | 0.358 | 326 |
|  | 3 | 9.37 | 16.2 | 0.337 | 315 |
|  | M | 9.69 | 13.43 | 0.34 | 343.33 |
|  | m | 0.74 | 3.03 | 0.021 | 39.93 |
|  | P | 0.5870064 | 0.7963124 | 0.9255417 | 0.5957544 |
| Lymphoma 16th day of | 1 | 10.15 | 12.8 | 0.321 | 307 |
|  | 2 | 9.17 | 16.6 | 0.315 | 384 |
|  | 3 | 9.36 | 13.9 | 0.339 | 349 |
|  | 4 | 10.58 | 14.9 | 0.336 | 357 |
|  | M | 9.82 | 14.55 | 0.33 | 349.25 |
|  | m | 0.66 | 1.61 | 0.010 | 31.90 |
|  | P | 0.70 | 0.15 | 0.17 | 0.32 |

| Animal group | Animal JVp | Color indicator | rhaemoglobin, g/l | SGE; pg | basophiles % |
|---|---|---|---|---|---|
| Healthy | 1 | 1.40 | 163 | 15.3 | 0 |
|  | 2 | 1.63 | 157 | 12.2 | 0 |
|  | 3 | 1.56 | 172 | 15.3 | 0 |
|  | 4 | 1.39 | 178 | 18.4 | 0 |
|  | 5 | 1.26 | 159 | 16.1 | 0 |
|  | 6 | 1.40 | 164 | 15.5 | 0 |
|  | 7 | 1.42 | 156 | 13.9 | 0 |
|  | 8 | 1.32 | 172 | 18.0 | 0 |
|  | 9 | 1.44 | 174 | 16.9 | 0 |
|  | 10 | 1.51 | 166 | 14.7 | 0 |
|  | 11 | 1.37 | 172 | 17.4 | 0 |
|  | M | 1.43 | 166.64 | 15.79 | 0.00 |
|  | m | 0.11 | 7.45 | 1.86 | 0.00 |
|  | P | 0.7555 | 0.2827 | 0.4990 | 0.5441 |

TABLE 3-continued

BLOOD TEST RESULTS

| | | | | | | |
|---|---|---|---|---|---|---|
| | Lymphoma | 1 | 1.23 | 148 | 14.3 | 0 |
| | | 2 | 1.18 | 153 | 16.0 | 0 |
| | | 3 | 1.05 | 146 | 16.3 | 0 |
| | | 4 | 1.36 | 149 | 13.2 | 0 |
| | | 5 | 1.29 | 152 | 14.4 | 0 |
| | | 6 | 1.09 | 158 | 18.5 | 0 |
| | | 7 | 1.58 | 163 | 13.6 | 0 |
| | | 8 | 1.22 | 135 | 12.0 | 0 |
| | | 9 | 1.12 | 146 | 15.3 | 0 |
| | | 10 | 0.96 | 144 | 17.5 | 0 |
| | | M | 1.21 | 149.40 | 15.12 | 0.00 |
| | | m | 0.18 | 7.75 | 2.01 | 0.00 |
| | | P | 0.0038 | 0.0001 | 0.44 | ### |
| | Lymphoma 5th | 1 | 1.29 | 158 | 15.6 | 0 |
| | day of observation | 2 | 1.13 | 146 | 15.3 | 0 |
| | | 3 | 1.01 | 143 | 16.3 | 0 |
| | | M | 1.14 | 149.00 | 15.72 | 0.00 |
| | | m | 0.14 | 7.94 | 0.52 | 0.00 |
| | | P | 0.540347 | 0.943144 | 0.4093296 | ### |
| | Lymphoma 10th | 1 | 1.17 | 138 | 13.1 | 0 |
| | day of observation | 2 | 1.10 | 149 | 16.3 | 0 |
| | | 3 | 1.07 | 142 | 15.2 | 0 |
| | | M | 1.12 | 143.00 | 14.84 | 0.00 |
| | | m | 0.05 | 5.57 | 1.60 | 0.00 |
| | | P | 0.1668929 | 0.1785296 | 0.818476 | ### |
| | Lymphoma | 1 | 1.20 | 146 | 14.4 | 0 |
| | 16th day of | 2 | 1.14 | 154 | 16.8 | 0 |
| | | 3 | 1.07 | 342 | 15.2 | 0 |
| | | 4 | 1.16 | 136 | 12.9 | 0 |
| | | M | 1.14 | 144.50 | 14.80 | 0.00 |
| | | m | 0.05 | 7.55 | 1.64 | 0.00 |
| | | P | 0.30 | 0.32 | 0.77 | #ΩΕJИΟΙ |

| Animal group | A. No | erythrocytes, $10^{12}$/l | nieukocytes, $10^9$/l | rhematocryte, l/l | thrombocytes $10^9$/l |
|---|---|---|---|---|---|
| Lymphoma + G | 1 | 10.26 | 14.3 | 0.338 | 318 |
| 14 5th day of | 2 | 9.98 | 13.0 | 0.329 | 329 |
| observation | 3 | 10.29 | 11.9 | 0.343 | 336 |
| | M | 10.18 | 13.07 | 0.34 | 327.67 |
| | m | 0.17 | 1.20 | 0.01 | 9.07 |
| | P | 0.715601 | 0.8668053 | 0.7595043 | 0.9575522 |
| Lymphoma + G | 1 | 9.88 | 11.9 | 0.316 | 297 |
| 14 10th day of | 2 | 11.12 | 10.2 | 0.342 | 365 |
| observation | 3 | 10.37 | 10.2 | 0.298 | 329 |
| | M | 10.456667 | 10.746667 | 0.3186667 | 330.33333 |
| | m | 0.6245265 | 0.9561555 | 0.0221209 | 34.019602 |
| | P | 0.4449097 | 0.0358157 | 0.2611622 | 0.9324813 |
| Lymphoma + G | 1 | 12.06 | 10.6 | 0.306 | 349 |
| 14th day of | 2 | 10.58 | 10.3 | 0.315 | 358 |
| observation | 3 | 9.85 | 9.5 | 0.345 | 337 |
| | 4 | 10.21 | 12.3 | 0.316 | 308 |
| | M | 10.68 | 10.6625 | 0.3205 | 338 |
| | m | 0.970 | 1.1832265 | 0.0169411 | 21.771541 |
| | P | 0.332247 | 0.029649 | 0.122879 | 0.535937 |

| Animal group | A.No | Color indicator | rhaemoglobin, g/l | SGE, pg | basophiles % |
|---|---|---|---|---|---|
| Lymphoma + G | 1 | 1.22 | 148 | 14.4 | 0 |
| 14 5th day of | 2 | 1.18 | 146 | 14.6 | 0 |
| observation | 3 | 1.30 | 157 | 15.3 | 0 |
| | M | 1.23 | 151.33 | 14.77 | 0.00 |
| | m | 0.06 | 5.86 | 0.43 | 0.00 |
| | P | 0.7074166 | 0.8332334 | 0.622176 | ### |
| Lymphoma + G | 1 | 1.26 | 158 | 16.0 | 0 |
| 14 10th day of | 2 | 1.43 | 160 | 14.4 | 0 |
| observation | 3 | 1.36 | 163 | 15.7 | 0 |
| | M | 1.3522984 | 160.33333 | 15.36627 | 0 |
| | m | 0.0884686 | 2.5166115 | 0.857753 | 0 |
| | P | 0.0965517 | 0.0029648 | 0.7638882 | ### |
| Lymphoma + G | 1 | 1.52 | 156 | 12.9 | 0 |
| 14th day of | 2 | 1.38 | 162 | 15.3 | 0 |
| observation | 3 | 1.26 | 158 | 16.0 | 0 |
| | 4 | 1.33 | 162 | 15.9 | 0 |
| | M | 1.3721048 | 159.5 | 15.03866 | 0 |
| | m | 0.1100269 | 3.01 | 1.4362455 | 0 |
| | P | 0.065395 | 0.004276 | 0.937102 | ### |

TABLE 3-continued

BLOOD TEST RESULTS

| Animal group | Animal JVp | Seosinophiles, % | metamyelocytesVo | Young neutrophiles % | Nuclear rod neutrophiles, % |
|---|---|---|---|---|---|
| Healthy | 1 | 3 | 0 | 0 | 2 |
|  | 2 | 1 | 0 | 0 | 3 |
|  | 3 | 3 | 0 | 0 | 1 |
|  | 4 | 2 | 0 | 0 | 3 |
|  | 5 | 3 | 0 | 0 | 4 |
|  | Q | 2 | 0 | 0 | 3 |
|  | 7 | 2 | 0 | 0 | 1 |
|  | 8 | 3 | 0 | 0 | 2 |
|  | 9 | 1 | 0 | *0 | 3 |
|  | 10 | 3 | 0 | 0 | 3 |
|  | 11 | 2 | 0 | 0 | 4 |
|  | M | 2.27 | 0.00 | 0.00 | 2.64 |
|  | m | 0.79 | 0.00 | 0.00 | 1.03 |
|  | P |  |  |  |  |
| Lymphoma | 1 | 2 | 3 | 16 | 76 |
|  | 2 | 2 | 3 | 21 | 72 |
|  | 3 | 3 | 4 | 20 | 69 |
|  | 4 | 4 | 2 | 12 | 79 |
|  | 5 | 3 | 1 | 18 | 75 |
|  | 6 | 3 | 3 | 16 | 76 |
|  | 7 | 2 | 2 | 21 | 73 |
|  | 8 | 1 | 3 | 27 | 65 |
|  | 9 | 1 | 2 | 16 | 78 |
|  | 10 | 3 | 3 | 19 | 71 |
|  | M | 2.40 | 2.60 | 18.60 | 73.50 |
|  | m | 0.97 | 0.84 | 4.06 | 4.09 |
|  | P | 0.75 | 0.93 | 0.00 | 0.00 |
| Lymphoma 5th day of observation | 1 | 2 | 3 | 15 | 76 |
|  | 2 | 1 | 2 | 17 | 78 |
|  | 3 | 3 | 2 | 22 | 70 |
|  | M | 2.00 | 2.33 | 18.00 | 74.67 |
|  | m | 1.00 | 0.58 | 3.61 | 4.16 |
|  | P | 0.5808337 | 0.5599376 | 0.8192365 | 0.6957082 |
| Lymphoma 10th day of observation | 1 | 2 | 1 | 18 | 75 |
|  | 2 | 2 | 3 | 15 | 76 |
|  | 3 | 1 | 3 | 18 | 75 |
|  | M | 1.67 | 2.33 | 17.00 | 75.33 |
|  | m | 0.58 | 1.15 | 1.73 | 0.58 |
|  | P | 0.1571958 | 0.7377703 | 0.3519747 | 0.1996915 |
| 15th day of | 1 | 3 | 3 | 13 | 77 |
|  | 2 | 2 | 2 | 15 | 75 |
|  | 3 | 1 | 2 | 18 | 74 |
|  | 4 | 1 | 1 | 18 | 76 |
|  | M | 1.75 | 2.00 | 16.00 | 75.50 |
|  | m | 0.96 | 0.82 | 2.45 | 1.79 |
|  | P | 0.30 | 0.27 | 0.18 | 0.19 |

| Animal group | Animal JVp | Segment rod neutrophiles % | Lymphocytes % | monocytes % | neutrophiles % |
|---|---|---|---|---|---|
| Healthy | 1 | 23 | 70 | 2 | 25 |
|  | 2 | 27 | 66 | 3 | 30 |
|  | 3 | 24 | 69 | 3 | 25 |
|  | 4 | 27 | 65 | 3 | 30 |
|  | 5 | 17 | 71 | 5 | 21 |
|  | Q | 27 | 65 | 3 | 30 |
|  | 7 | 25 | 68 | 4 | 26 |
|  | 8 | 23 | 69 | 3 | 25 |
|  | 9 | 26 | 67 | 3 | 29 |
|  | 10 | 25 | 66 | 3 | 28 |
|  | 11 | 26 | 65 | 3 | 30 |
|  | M | 24.55 | 67.36 | 3.18 | 27.18 |
|  | m | 2.91 | 2.16 | 0.75 | 2.99 |
|  | P |  |  |  |  |
| Lymphoma | 1 | 16 | 76 | 3 | 19 |
|  | 2 | 21 | 72 | 2 | 24 |
|  | 3 | 20 | 69 | 4 | 24 |
|  | 4 | 12 | 79 | 3 | 14 |
|  | 5 | 18 | 75 | 3 | 19 |
|  | 6 | 16 | 76 | 2 | 19 |
|  | 7 | 21 | 73 | 2 | 23 |
|  | 8 | 27 | 66 | 3 | 30 |
|  | 9 | 16 | 78 | 3 | 18 |

TABLE 3-continued

BLOOD TEST RESULTS

|  |  |  |  |  |  |
|---|---|---|---|---|---|
|  |  | 10 | 19 | 71 | 4 | 22 |
|  |  | M | 18.60 | 73.50 | 2.90 | 21.20 |
|  |  | m | 4.06 | 4.09 | 0.74 | 4.39 |
|  |  | P | 0.00 | 0.00 | 0.40 | 0.00 |
| Lymphoma | 1 | 15 | 76 | 4 | 18 |
| 5th day of | 2 | 17 | 78 | 2 | 19 |
| observation | 3 | 19 | 70 | 6 | 21 |
|  | M | 17.00 | 74.67 | 4.00 | 19.33 |
|  | m | 2.00 | 4.16 | 2.00 | 1.53 |
|  | P | 0.3831484 | 0.6957082 | 0.4424511 | 0.2824126 |
| Lymphoma 10th | 1 | 16 | 23 | 8 | 17 |
| day of | 2 | 15 | 71 | 9 | 18 |
| observation | 3 | 14 | 75 | 7 | 17 |
|  | M | 15.00 | 73.00 | 8.00 | 17.33 |
|  | m | 1.00 | 2.00 | 1.00 | 0.58 |
|  | P | 0.026685 | 0.7808126 | 0.0056274 | 0.0221896 |
| 15th day of | 1 | 13 | 77 | 4 | 16 |
|  | 2 | 15 | 75 | 6 | 17 |
|  | 3 | 18 | 68 | 11 | 20 |
|  | 4 | 17 | 72 | 9 | 18 |
|  | M | 15.75 | 73.00 | 7.50 | 17.75 |
|  | m | 2.22 | 3.92 | 3.11 | 1.71 |
|  | P | 0.12 | 0.84 | 0.06 | 0.06 |

| Animal group | Animal No | Eosinophiles % | metamyelocytes % | Young neutrophiles % | Nuclear rod neutrophiles, % |
|---|---|---|---|---|---|
| Lymphoma + G | 1 | 2 | 2 | 18 | 75 |
| 145th day of observation | 2 | 2 | 3 | 19 | 71 |
|  | 3 | 1 | 2 | 26 | 69 |
|  | M | 1.67 | 2.33 | 21.00 | 71.67 |
|  | m | 0.58 | 0.58 | 4.36 | 3.06 |
|  | P | 0.1571958 | 0.5599376 | 0.4556646 | 0.4446301 |
| Lymphoma + G | 1 | 1 | 3 | 20 | 72 |
| 14 10th day of observation | 2 | 2 | 3 | 25 | 66 |
|  | 3 | 2 | 2 | 26 | 68 |
|  | M | 1.67 | 2.67 | 23.67 | 68.67 |
|  | m | 0.577 | 0.577 | 3.214 | 3.055 |
|  | P | 0.1571958 | 0.8820888 | 0.0855304 | 0.0848905 |
| Lymphoma + G | 1 | 2 | 2 | 24 | 68 |
| 14th day of | 2 | 2 | 2 | 27 | 66 |
| observation | 3 | 3 | 3 | 19 | 73 |
|  | 4 | 4 | 3 | 25 | 65 |
|  | M | 2.75 | 2.5 | 23.75 | 68.0 |
|  | m | 0.957 | 0.577 | 3.403 | 3.56 |
|  | P | 0.561758 | 0.805340 | 0.048093 | 0.044019 |

| Animal group | Animal No | Segment rod neutrophiles % | Lymphocytes, % | monocytes % | neutrophiles % |
|---|---|---|---|---|---|
| Lymphoma + G | 1 | 13 | 75 | 8 | 15 |
| 145th day of observation | 2 | 16 | 71 | 8 | 19 |
|  | 3 | 23 | 69 | 5 | 25 |
|  | M | 17.33 | 71.67 | 7.00 | 19.67 |
|  | m | 5.13 | 3.06 | 1.73 | 5.03 |
|  | P | 0.72279 | 0.4446301 | 0.0480755 | 0.6667086 |
| Lymphoma + G | 1 | 15 | 72 | 9 | 18 |
| 14 10th day of observation | 2 | 20 | 66 | 9 | 23 |
|  | 3 | 19 | 68 | 9 | 21 |
|  | M | 18.01 | 68.7 | 9.0 | 20.7 |
|  | m | 2.645 | 3.05 | 0 | 2.52 |
|  | P | 0.7752258 | 0.0848905 | 8.462E−10 | 0.7993774 |
| Lymphoma + G | 1 | 20 | 68 | 8 | 22 |
| 14th day of | 2 | 19 | 66 | 11 | 21 |
| observation | 3 | 16 | 73 | 5 | 19 |
|  | 4 | 23 | 65 | 5 | 26 |
|  | M | 19.5 | 68.0 | 7.25 | 22.0 |
|  | m | 2.89 | 3.56 | 2.872 | 2.94 |
|  | P | 0.653787 | 0.044019 | 0.054445 | 0.702377 |

| Animal group | Animal JVp | neutrophiles/ lymphocytes | Total protein; gl | LDH, U/L | Body weight, g | lymphocytes, $10^9$/n |
|---|---|---|---|---|---|---|
| SflopoBbie | 1 | 0.36 | 60.3 | 370 |  | 6.02 |
|  | 2 | 0.45 | 56.8 | 519 |  | 7.21 |
|  | 3 | 0.36 | 60.3 | 487 |  | 6.23 |
|  | 4 | 0.46 | 54.2 | 467 |  | 6.44 |
|  | 5 | 0.30 | 53.9 | 469 |  | 7.35 |

TABLE 3-continued

BLOOD TEST RESULTS

|  |  |  |  |  |  |  |
|---|---|---|---|---|---|---|
|  | 6 | 0.46 | 56.5 | 423 |  | 6.72 |
|  | 7 | 0.38 | 56.3 | 487 |  | 6.79 |
|  | 8 | 0.36 | 55.2 | 387 |  | 6.02 |
|  | 9 | 0.43 | 54.8 | 472 |  | 6.16 |
|  | 10 | 0.42 | 56.7 | 406 |  | 6.23 |
|  | 11 | 0.46 | 53.2 | 398 |  | 6.72 |
|  | M | 0.41 | 56.20 | 444.09 |  | 6.54 |
|  | m | 0.06 | 2.36 | 48.98 |  | 0.46 |
|  | P |  |  |  |  |  |
| JHM(DO)Ma Hanano onbixa | 1 | 0.25 | 52.8 | 984 | 18.06 | 10.36 |
|  | 2 | 0.33 | 51.5 | 1298 | 18.15 | 8.82 |
|  | 3 | 0.35 | 54.8 | 1147 | 18.27 | 6.51 |
|  | 4 | 0.18 | 52.6 | 1289 | 19.29 | 8.33 |
|  | 5 | 0.25 | 55.1 | 1157 | 18.57 | 8.96 |
|  | 6 | 0.25 | 52.3 | 1079 | 19.86 | 11.55 |
|  | 7 | 0.32 | 49.7 | 1457 | 18.51 | 9.03 |
|  | 8 | 0.45 | 54.8 | 1287 | 18.23 | 7.49 |
|  | 9 | 0.23 | 53.2 | 1229 | 18.27 | 9.03 |
|  | 10 | 0.31 | 53.1 | 1362 | 18.51 | 10.22 |
|  | M | 0.29 | 52.99 | 1228.90 | 18.57 | 9.03 |
|  | m | 0.08 | 1.66 | 139.77 | 0.57 | 1.45 |
|  | P | 0.00 | 0.0019080 | 0.000000025 | ### | 0.00032 |
| JFM(DO)Ma 5 пВНb Haбjm.=HHfl | 1 | 0.24 | 48.9 | 1364 | 18.06 | 10.64 |
|  | 2 | 0.24 | 53.4 | 1147 | 18.04 | 8.26 |
|  | 3 | 0.30 | 55.6 | 1078 | 18.12 | 9.52 |
|  | M | 0.26 | 52.63 | 1196.33 | 18.07 | 9.473333 |
|  | m | 0.03 | 3.42 | 149.25 | 0.04 | 1.190686 |
|  | P | 0.3396658 | 0.8754870 | 0.7578670 | 0.0220475 | 0.433866 |
| JHM(DO)Ma 10 HaSpraeHHfl | 1 | 0.23 | 48.7 | 1285 | 17.89 | 7.14 |
|  | 2 | 0.25 | 51.6 | 1197 | 18.15 | 9.73 |
|  | 3 | 0.23 | 53.5 | 1307 | 18.24 | 11.34 |
|  | M | 0.24 | 51.27 | 1263.00 | 18.09 | 9.40 |
|  | m | 0.01 | 2.42 | 58.21 | 0.18 | 2.12 |
|  | P | 0.0595633 | 0.3430529 | 0.5544080 | 0.0431143 | 0.796312 |
| 1 Grsrn | 1 | 0.21 | 53.8 | 1256 | 18.02 | 8.96 |
|  | 2 | 0.23 | 46.5 | 1203 | 17.34 | 11.62 |
|  | 3 | 0.29 | 51.6 | 1115 | 18.16 | 9.73 |
|  | 4 | 0.25 | 50.4 | 1382 | 18.23 | 10.43 |
|  | M | 0.24 | 50.58 | 1239 | 17.94 | 10.19 |
|  | m | 0.04 | 3.06 | 87.48 | 0.41 | 1.13 |
|  | P | 0.15 | 0.21 | 0.48 | 0.05 | 0.15 |

| Animal group | Anumal No | neutrophiles/lymphocytes | Total protein g/l | LDH, U/L | Body, weight, g | Lymphocytes, 10% |
|---|---|---|---|---|---|---|
| JHD(D>OMa+ G143 BBRi HaGjC3n-HHSl | 1 | 0.20 | 51.5 | 1056 | 18.27 | 10.01 |
|  | 2 | 0.27 | 52.6 | 974 | 17.86 | 9.1 |
|  | 3 | 0.36 | 56.8 | 856 | 18.00 | 8.33 |
|  | M | 0.28 | 53.63 | 962.00 | 18.04 | 9.15 |
|  | m | 0.08 | 2.80 | 100.54 | 0.21 | 0.84 |
|  | P | 0.7875676 | 0.7352820 | 0.0166465 | 0.035003 | 0.866805 |
| BHM(D>OMa+ 0 14 10 sHb HaSjtroeHHfi | 1 | 0.25 | 52.9 | 698 | 18.28 | 8.295 |
|  | 2 | 0.35 | 54.5 | 753 | 18.36 | 7.112 |
|  | 3 | 0.31 | 56.8 | 798 | 17.97 | 7.161 |
|  | M | 0.3024361 | 54.733333 | 749.66666 | 18.203333 | 7.522667 |
|  | m | 0.0495521 | 1.9604421 | 50.083264 | 0.2059935 | 0.669309 |
|  | P | 0.79587 | 0.2589797 | 3.684E-06 | 0.1184878 | 0.035816 |
| DHM(D>OMa+ 0 14 160cHb Baбjm ncfH>i | 1 | 0.32 | 56.5 | 759 | 18.53 | 7.413 |
|  | 2 | 0.32 | 57.8 | 583 | 18.12 | 7.182 |
|  | 3 | 0.26 | 59.7 | 697 | 18.26 | 6.65 |
|  | 4 | 0.40 | 56.5 | 653 | 18.60 | 8.61 |
|  | M | 0.3254963 | 57.625 | 673 | 18.3775 | 7.46375 |
|  | m | 0.0573356 | 1.5129992 | 74.099032 | 0.2257395 | 0.828259 |
|  | P | 0.404205 | 0.002249 | 0.000002 | 0.378400 | 0.02965 |

Notes

Figure 6:
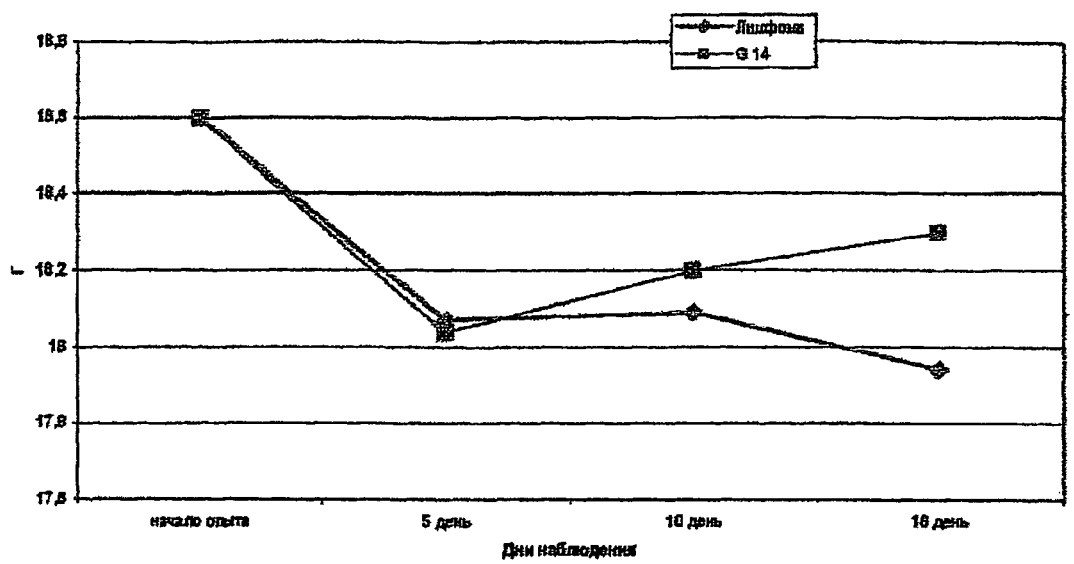
FIG. 6 is a graph showing a changes in body weight between diseased, untreated mice and mice treated with a compound of formula (I).

1) M - (function <<averarithmetic>> - appendix Exel for MsOffice XP);
2) m - average arithmetic error (standard deviation-function <<standrddev>> - appendix Exel for MsOffice XP);
3) P - Student's reliability coefficient (reliability level-95%) - function <<T-test>> - appendix Exel for MsOffice XP;
4) ### - Student's reliability coefficient has not been counted as parameters values equal to 0 (metamyelocytes, young neutrophiles and basophiles might not be found in leukogramma made by counting of 200 cells per smear, but this is quite a norm for white mice).
5) P - fljia >KMBOTHbix c nuMdpoMoii paccHMTbieanacb no KomponbHoi/i rpynne; P - fLjin XMBOTHbix c muMdpoMOM + npenapai Libanus cedra G 14 paccHMTbiBanocb no rpynne CJIl/IMCpOMOiL By day 16 of the study, significant differences in body weight of animals between the groups were observed; in mice treated with 24-ethyl-cholestane-3β,5α,6α-triol, there was a tendency to a gain in mass (FIG. 6).

Figure 7:
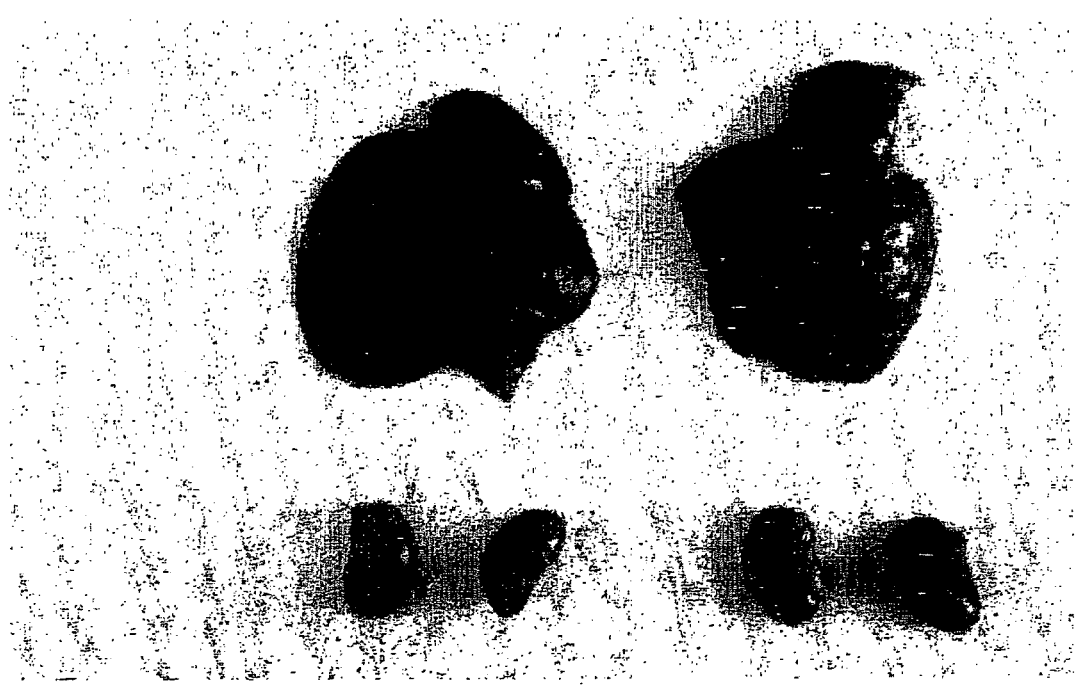
FIG. 7 is a photograph showing organs in healthy mice (right) and in mice with lymphoma (left) treated with a compound of the invention for sixteen days.
Figure 8:
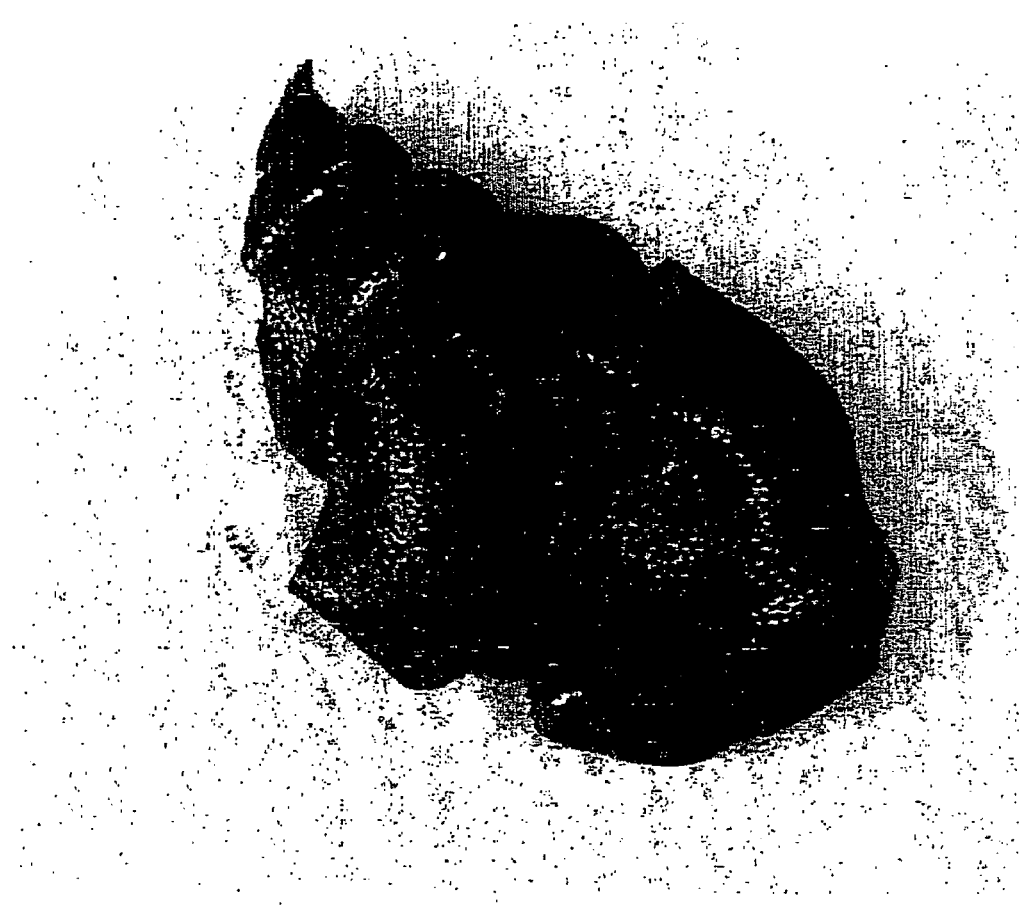
FIG. 8 is a photograph showing toxic lesions in the liver of an treated mouse with lymphoma.
Figure 9:
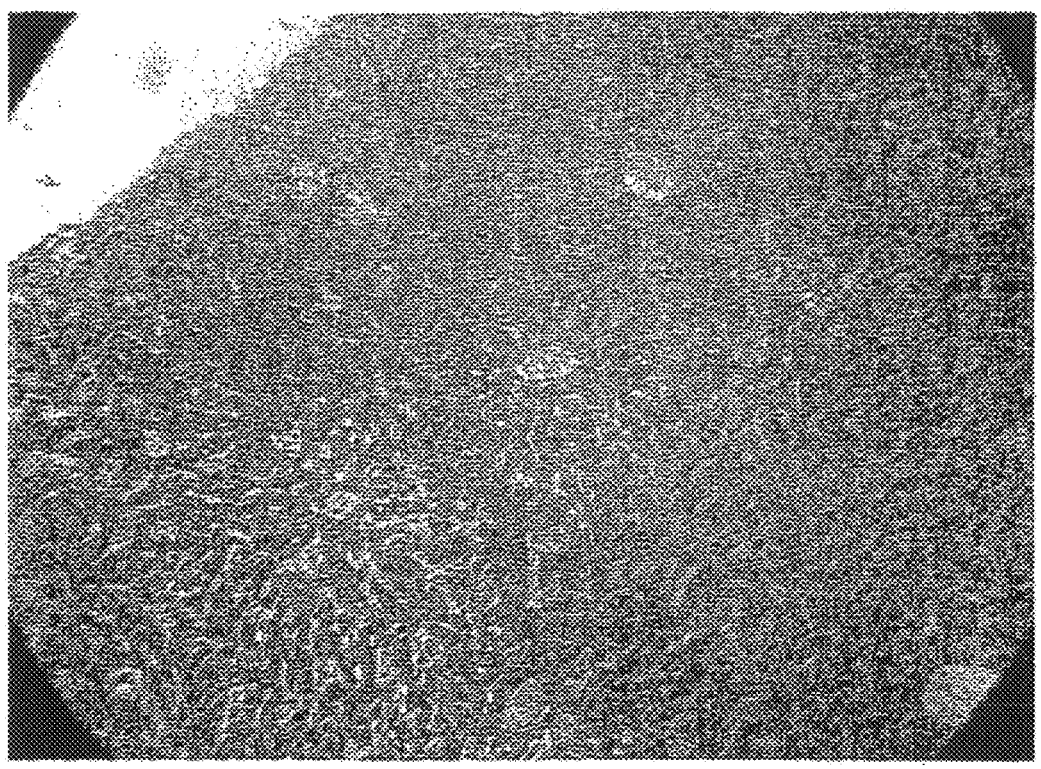
FIG. 9 is a photomicrograph (450×) of part of the liver taken from a mouse with experimental lymphoma, showing extensive lymphocytic proliferation and granuloma.
Figure 10:
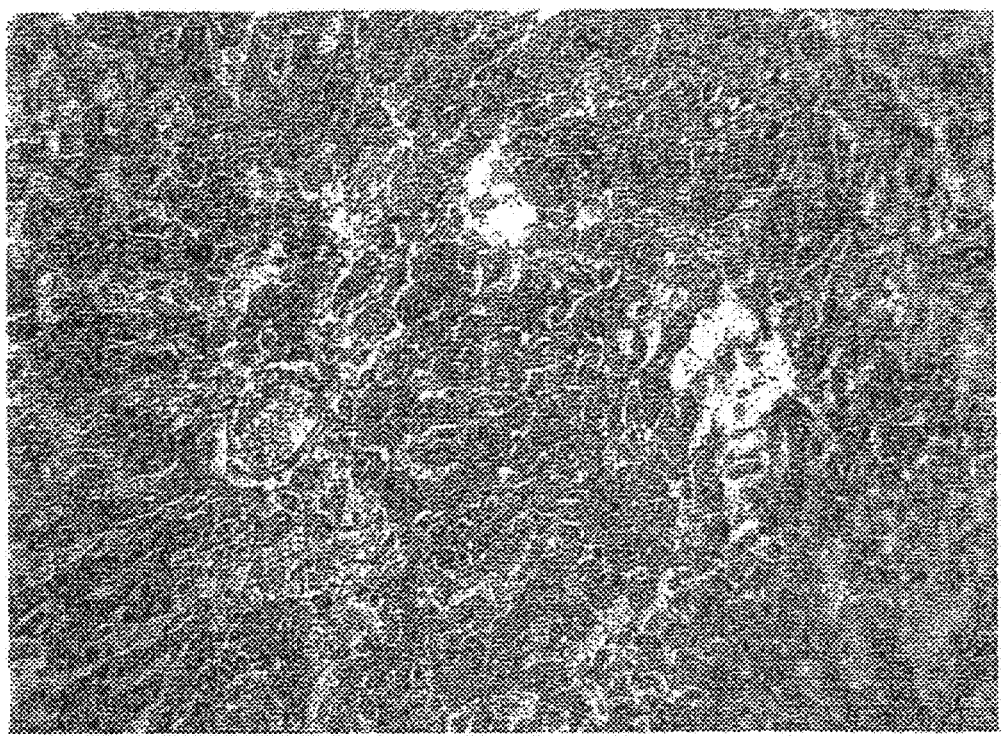
FIG. 10 is a photomicrograph (900×) of part of the liver taken from a mouse with experimental lymphoma, showing extensive lymphocytic granuloma.
Figure 11:
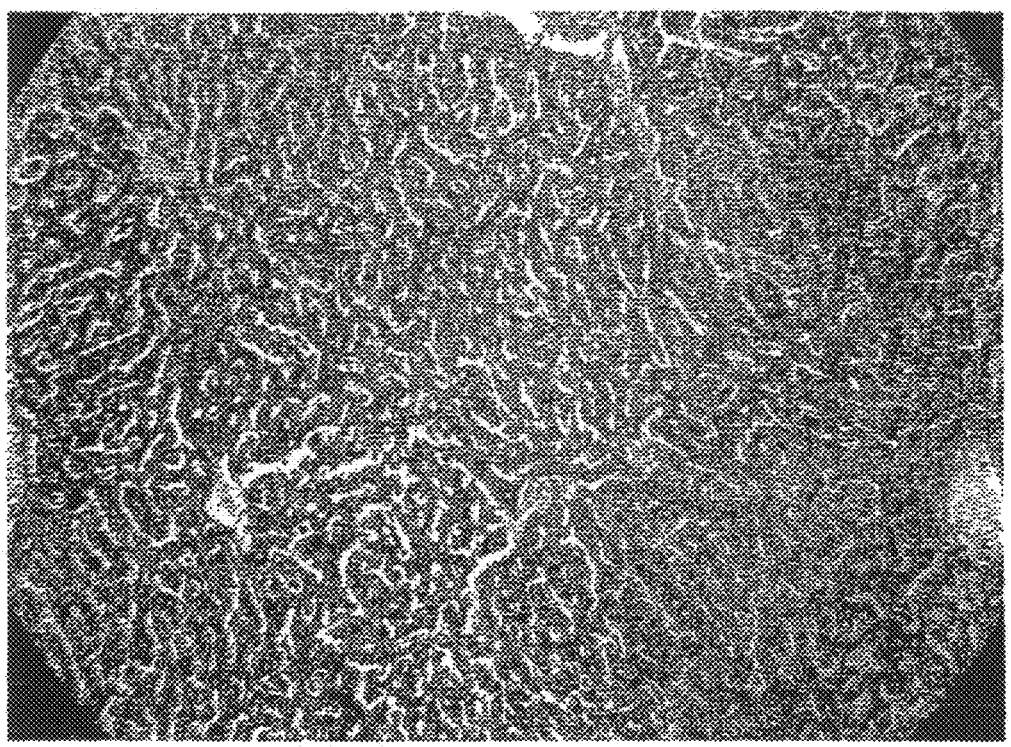
FIGS. 11 and 12 are photomicrographs (450× and 900×, respectively) of part of the liver taken from a mouse with experimental lymphoma orally administered 24-ethyl-cholestane-3β,5α,6α-triol daily at a dosage of 250 mg/kg. Lymphocytic proliferation is insignificant.
Figure 12:
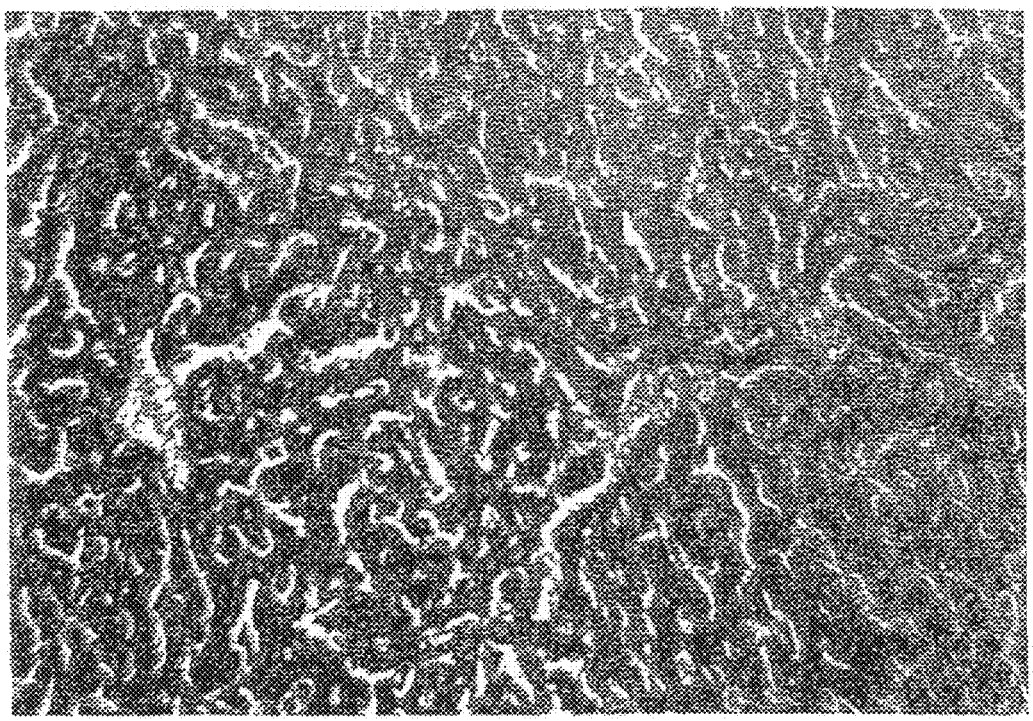
Figure 13:
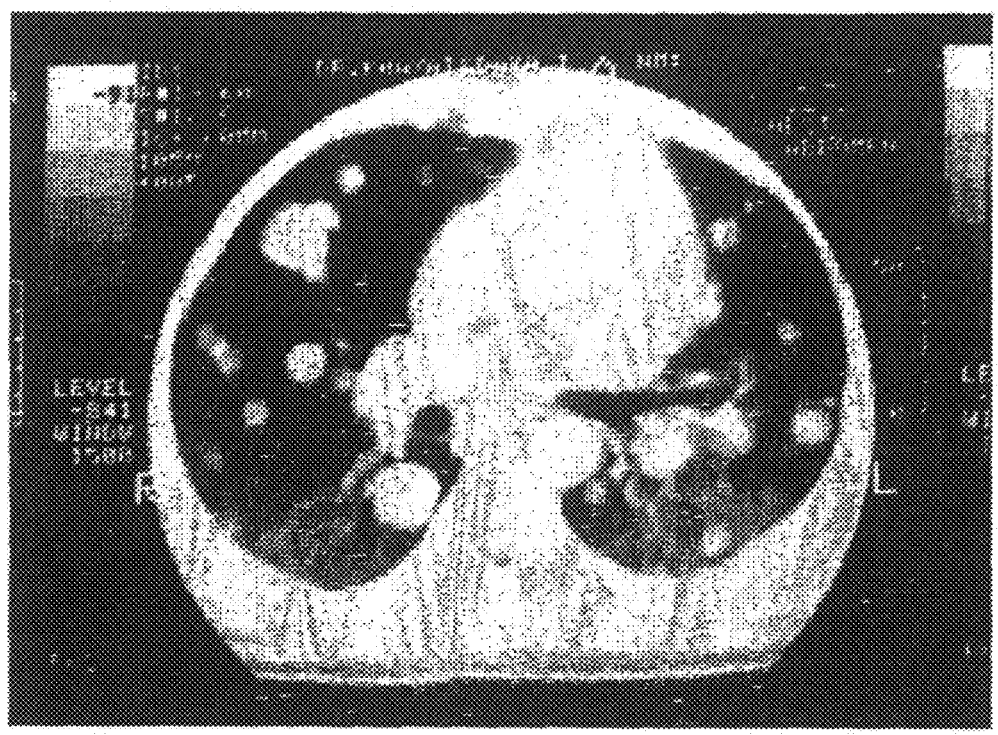
FIGS. 13 and 14 are CT scans showing a non small cell lung cancer before treatment (FIG. 13) and the same cut after treatment (FIG. 14) for 9 months using the compound of formula II.
Figure 14:
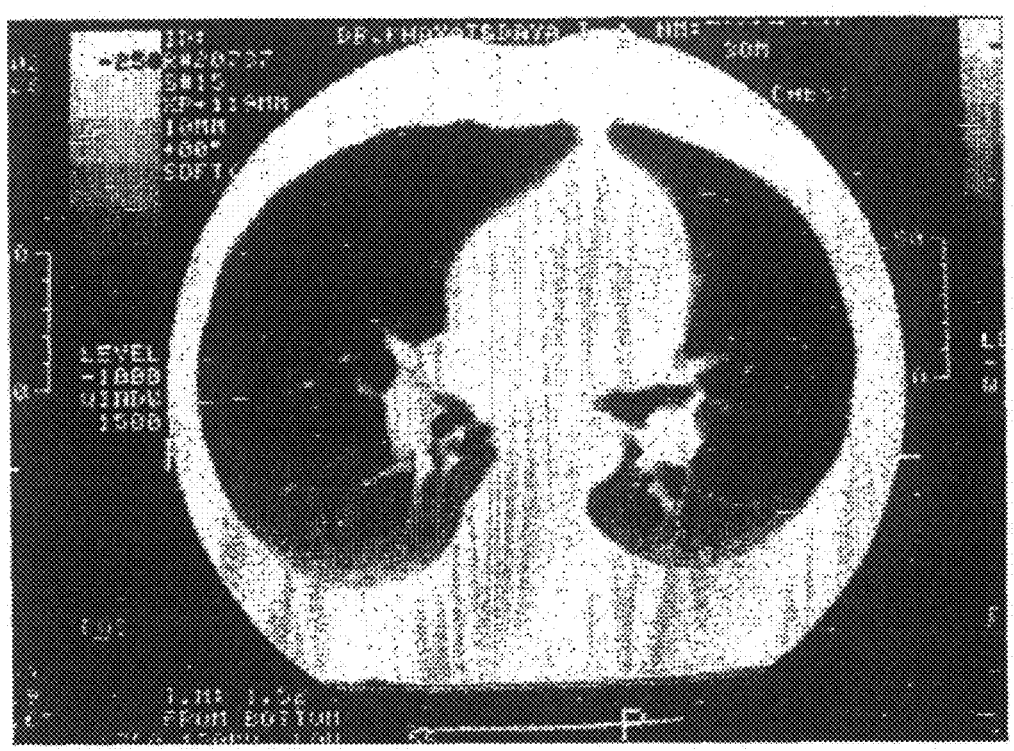
Figure 15:
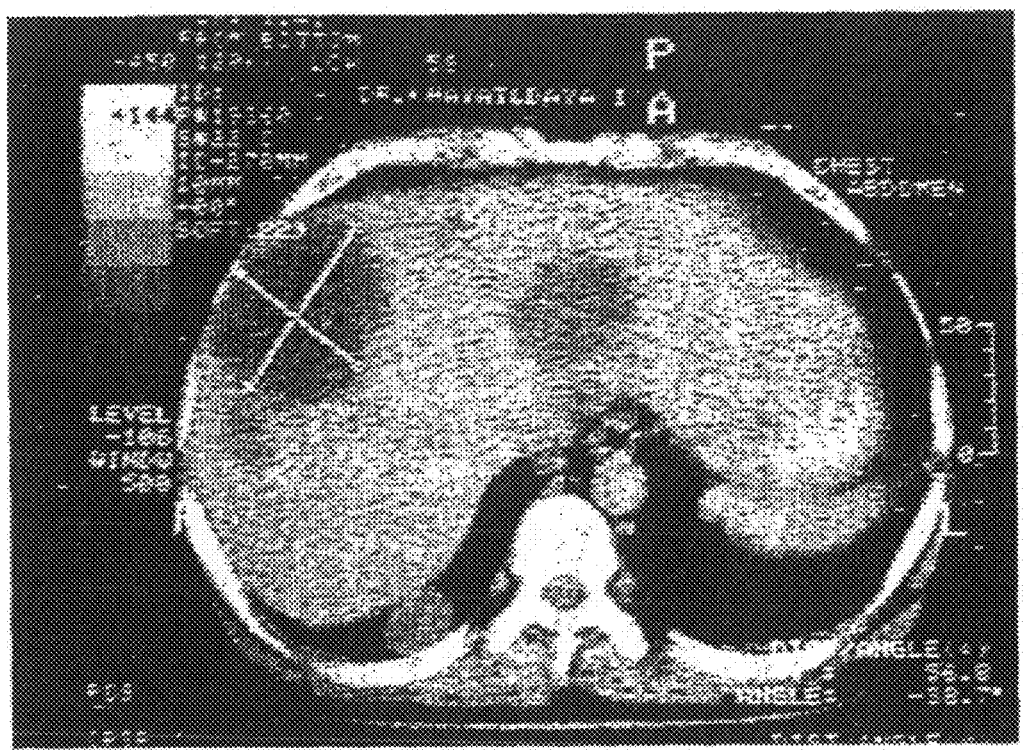
FIGS. 15 and 16 are CT scans showing a non small cell lung cancer metastatic to liver before treatment FIG. 15) and after treatment (FIG. 16) for 9 months using the compound of formula II.
Figure 16:
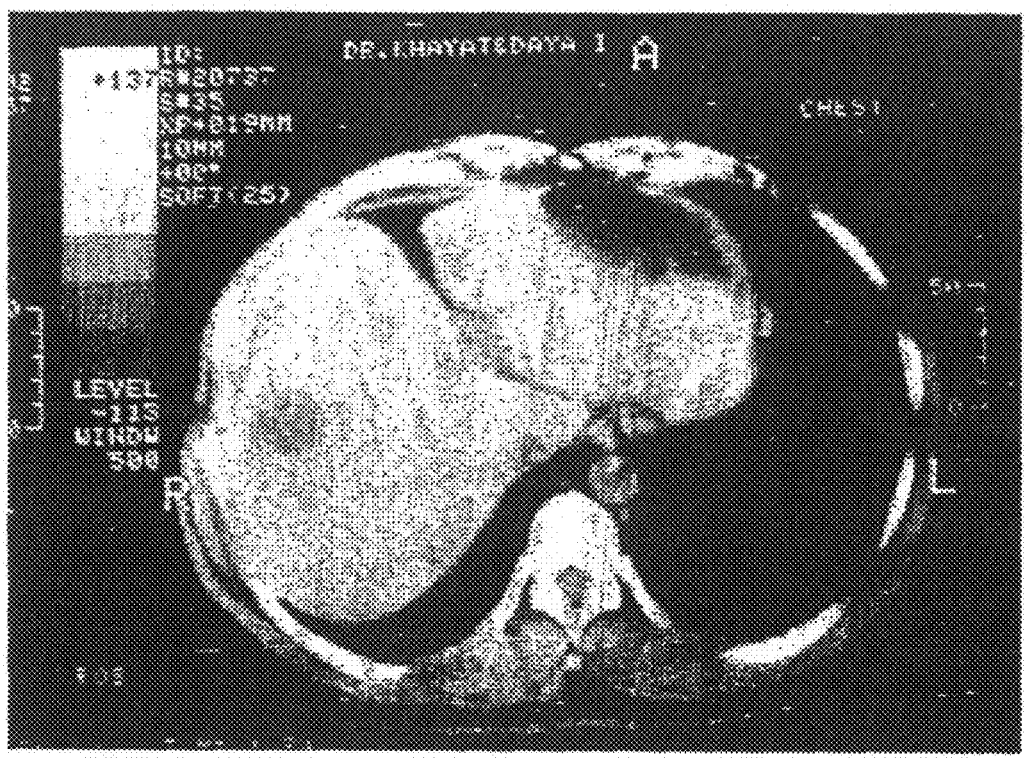

An autopsy investigation revealed no differences between animals with lymphoma treated with 24-ethyl-cholestane-3β, 5α,6α-triol and healthy mice. Liver, kidney, and spleen tissues showed no differences (FIG. 7). In contrast, in three animals receiving no medication displayed macroscopic morphological changes (FIG. 8).

Example 2

Assessment of the Therapeutic Efficacy of 24-ethyl-cholestane-3β,5α,6α-triol on Human Tumor Cell Lines in Mice Immunocompromised mice were used for this experiment. Mice were inbred in a sterile environment and fed ad libitum. Four groups of 40 mice, weighing approximately 20 g each (range: 17-25 g), were used for each tumor type. The human tumor cell lines used were the following: large B-cell lymphoma; squamous-cell carcinoma of the lung; ductal carcinoma breast; and adenocarcinoma of the lung. A suspension of tumor cells was injected in the peritoneum of immunocompromised mice. Following this, mice were examined and weighed daily. After 6-8 days, we observed the development of abdominal carcinomatosis and ascitis. At day 18, we observed the development of an abundant ascitis, which increased the weight of the mice by approximately 20 g. At that time, mice were divided into four groups of 10. One group of 10 mice was used as control and did not receive any medication. The other three groups were treated respectively with 4, 2 and 0.8 mg/kg/day of 24-ethyl-cholestane-3β,5α,6α-triol administered orally for 10 days. Assessment of tumor cell concentration in the ascitis and abdominal metastases were measured on day 18 and every 2 days thereafter.

In all mice, prior to treatment, we observed an increase in LDH ESR (>100) and a decrease in the hematocrit. Control (untreated) mice all died between day 21 and day 25 in all tumor types. Dead mice were examined and showed abdominal carcinoinatosis associated with lymph nodes and liver metastases.

Our observations of treated mice are summarized in Table 4.

TABLE 4

|  | Breast CA | Lymphoma | Squamous lung | Adenocarcinonia |
|---|---|---|---|---|
| Complete Remission | 60% | 80% | 50% | 40% |
| Partial Remission | 20% | 10% | 30% | 20% |
| Stable Disease | 20% | 10% | 20% | 30% |
| Progressive Disease | 0% | 0% | 0% | 10% |
| Symptomatic Response | 100% | 100% | 100% | 100% |

Complete response: Weight (and ascetic) loss and the disappearance of all abdominal metastatic nodules and tumor cells.
Partial response: Weight (and ascitic) loss and at least 25% decrease of tumor cell in the ascitis with at least 25% decrease in measured abdominal metastatic nodules.
Stable disease: When tumor regression and or tumor cells in the ascitic fluid did not regress by at least 25%.
Progressive disease: When we observed an increase in ascitis or tumor volume or death of the animal.
Symptomatic response: Improvement in the general condition of mice with decrease in LDH, normalization of ESR and of hematocrit level.

Furthermore we observed in most of the treated mice: (1) a rapid response to therapy (ascitic regression within 1-2 days); (2) a total clearance of tumor cells associated with an important tumor lysis; (3) a normalization of hematological abnormalities; and (4) an improvement in the general condition. Additionally, we observed a three month survival without recurrence in mice that exhibited a complete response.

Example 3

Treatment of a Metastatic Renal Cell Carcinoma with 24-ethyl-cholestane-3β,6α-triol A 45-year old male patient presented with a metastatic renal cell carcinoma (stage IV), including an 8 cm tumor in the left kidney associated with multiple bilateral lung metastases (1.5-2 cm size). Pathology revealed a sarcomatoid renal cell carcinoma (grade 4/4). A left nephrectomy was performed, followed by interferon therapy for 6 weeks. Two months later, a chest CT scan reveals persistence of one metastatic deposit 1 cm in size in both lungs. At this point, the patient is administered 24-ethyl-cholestane-3β,5α,6α-triol (80 mg/day). Six weeks later, a chest CT scan reveals a disappearance of the left lung metastasis. Eight months later, another chest CT scan revealed one 1 mm nodule in the right lower lobe. One year after commencing therapy, the chest CT scan appeared normal.

Example 4

Treatment of Hormone Resistant Metastatic Prostate Cancer with 24-ethyl-cholestane-3β,5α,6α-triol A 75-year old male patient presented with hormone resistant metastatic prostate cancer. He had previously been treated with three courses of chemotherapy (Navelbine+Taxotere, but his PSA was still increasing. Administration of 24-ethyl-cholestane-3β,5α,6α-triol was commenced (70 mg/day).

The patient's PSA history is shown in Table 5.

TABLE 5

| PSA | |
|---|---|
| Day 0 (prior to treatment) | 1958 (nl < 4) |
| Day 13 | 1590 |
| Day 15 | 1142 |
| Day 67 | 802 |
| Day 110 | 772 |

The patient died in May 2005 due to a severe pneumonia unrelated to his cancer.

Example 5

Treatment of Breast Carcinoma with 24-ethyl-cholestane-3β,5α,6α-triol

A 46 YO female patient with a past medical history of anemia and mild chronic renal failure due to retroperitoneal fibrosis presented with a stage IV poorly differentiated lobular carcinoma of the right breast and liver, spleen and bone metastases. After many hormonal treatments with tamoxifen, zoladex and arimidex, she had a liver progression. Treatment with 24-ethyl-cholestane-3β,5α,6α-triol was commenced (60 mg/day). Three days after treatment, we observed a decrease in LDH level from 450 to 204. Five months after treatment commenced, liver enzymes including LDH returned to normal and her markers decreased as shown in Table 6:

TABLE 6

|  | CA 15-3 | CA 125 |
| --- | --- | --- |
| Before LC | 237 | 125 |
| After LC | 86 | 69 |

Her spleen metastasis has regressed on CT scan and the primitive breast mass has also regressed on ultrasound from 5 to 3 cm. Renal failure and anemia both improved, and a total Body MRI showed a complete liver and spleen response.

Example 6

Treatment of Uterine Cancer with
24-ethyl-cholestane-3β,5α,6α-triol

A 49 year-old female patient presented with uterine cancer stage IIB. She previously received cisplatin-based chemotherapy and radiotherapy. A pelvic MRI showed a recurrent 3.2 cm pelvic mass+retroperitoneal lymph nodes. A cervical biopsy confirms the recurrence.

Administration with 24-ethyl-cholestane-3β,5α,6α-triol was commenced (60 mg/day). Within three months, the tumor had disappeared on clinical exam and abdomino-pelvic CT scan.

Example 7

Treatment of Squamous Cell Lung Carcinoma with
24-ethyl-cholestane-3β,5α,6α-triol A 67 year-old female patient with presented with a left squamous-cell carcinoma of the lung. She commenced therapy with 24-ethyl-cholestane-3β,5α,6α-triol (50 mg/day) and experienced a drastic and rapid improvement in her general condition. Seven months later the patient received radiotherapy to the left lung. Nine months after commencing treatment, the patient has considerable improvement and significant regression of the left lung opacity, with a persistence of a small stellate image around the left superior bronchus. Fourteen months after therapy commenced, the patient fibroscopy is normal, and the dose of 24-ethyl-cholestane-3β, 5α,6α-triol is reduced to 30 mg/day. A fibroscopy later that year shows a compression on the left superior lobular bronchus, and the dose of 24-ethyl-cholestane-3β,5α,6α-triol is increased to 50 mg/day. Nearly five years after commencement of therapy, there is recurrence of the left lung tumor. The patient undergoes a left pneumonectomy and drug therapy is stopped, but the tumor recurs and the patient dies.

Example 8

Treatment of Lung Large-cell Adenocarcinoma with
24-ethyl-cholestane-3β,5α,6α-triol A 26 year-old male patient was diagnosed with a lung large-cell adenocarcinoma metastatic to liver. He received chemotherapy with no success. The patient was administered 24-ethyl-cholestane-3β,5α,6α-triol (70 mg/day). He also had frequent hemoptysis and elevated LDH, GGT, and bilirubin. The course of the patient's biologic parameters during treatment are depicted in Table 7. In addition to these data, GGT also fell to 31.

TABLE 7

|  | LDH | Total Bilirubin |
| --- | --- | --- |
| Day 0 (prior to treatment) | 2560 (nl < 480) | 1.9 (nl < 1) |
| Day 11 | 2264 | ND |
| Day 30 | 283 | ND |
| Day 63 | 118 | 0.42 |
| Day 85 | 230 | 0.37 |

More than a year after commencement of therapy, the patient's CT scans show a decrease in number and size of previous masses seen in the lungs and liver (FIGS. 13-16).

Example 9

Treatment of Breast Cancer with
24-ethyl-cholestane-3β,5α,6α-triol

A 36 year-old female patient presented with breast cancer stage IV with lung and bone metastases. She previously underwent a left radical mastectomy for a stage 2 colloidal mucinous adenocarcinoma Hormone receptors and c-erb B were negative. She received adjuvant chemotherapy (FAC) followed by radiotherapy. Later, a sternal bone metastasis appeared and was resected. The pathology revealed an adenocarcinoma with positive hormone receptors. She also developed lung metastases up to 4 cm size. She received chemotherapy with taxotere, navelbine, and pamidronate, followed by tamoxifen. This treatment gave an almost complete response in the lungs. Tamoxifen was replaced by Femara. The patient received radiotherapy on the spine (T4 and T1 2) and Zometa is administered along with Femara. However, there is progression of bone metastases on bone scan, and a chest CT scan reveals stable lung metastases.

Therapy with 24-ethyl-cholestane-3β,5α,6α-triol is commenced (60 mg/day), when the CA 15-3 marker was at 227 U. Zometa and Femara were continued and Decapeptyl was added to the treatment.

The course of CA 15-3 is shown in Table 8.

TABLE 8

| Month 0 (prior to treatment) | 277 (nl < 35) |
| --- | --- |
| Month 5 | 156 |
| Month 6 | 85 |
| Month 6 | 52 |
| Month 14 | 24 |
| Month 16 | 19.5 |

Two weeks after the beginning of LC, the patient was totally asymptomatic.

Example 10

Treatment of Pancreatic Cancer with
24-ethyl-cholestane-3β,5α,6α-triol

A 68 year-old diabetic and insulin dependent male patient with a past history of lymphoma presented with a 3 cm tumor in the head of pancreas and a suspicion of hepatic metastasis. An open biopsy of the pancreas revealed a moderately differentiated adenocarcinoma. Therapy with 24-ethyl-cholestane-3β,5α,6α-triol was commenced (50 mg/day). The course of CA 19-9 is shown in Table 9.

TABLE 9

| | |
|---|---|
| Day 0 (prior to treatment) | 884 (nl < 37) |
| Day 1 | 793 |
| Day 32 | 675 |
| Day 59 | 1127 |
| Day 128 | 545 |

On Day 59, the dose of 24-ethyl-cholestane-3β,5α,6α-triol was increased to 60 mg/day because CA 19-9 levels were increasing. A CT scan of the abdomen performed on Day 200 of therapy revealed an atrophic pancreas with no masses seen, a normal liver, and multiples lymph nodes in the peri-aortic and mesenteric areas.

Example 11

Histological Analysis of Therapeutic Efficacy of 24-ethyl-cholestane-3β,5α,6α-triol in Mice with Experimental Lymphoma Parenchymatous organs liver and kidneys received from mice with experimental lymphoma on the 15th day of observation and from mice treated with 24-ethyl-cholestane-3β,5α,6α-triol were taken for the histological analysis. Micropreparations were stained with hematoxilin eosin and examined by microscopy (FIGS. 9, 10, 11, and 12).

Other Embodiments

All publications, patent applications including U.S. Patent Application No. 60/741,725, filed Dec. 2, 2005, and patents cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating a cancer selected from the group consisting of lymphoma, large B-cell lymphoma, squamous-cell lung carcinoma, breast carcinoma, adenocarcinoma of the lung, renal cell carcinoma, prostate cancer, uterine cancer, pancreatic cancer, and non-small cell lung cancer, said method comprising administering a cancer treating amount of a compound described by the formula (I):

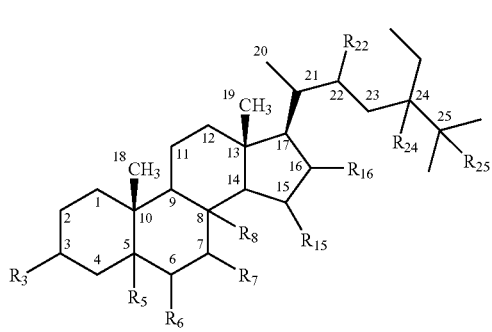

(I)

wherein
each of $R_3$, $R_5$, and $R_6$ is, independently, selected from OH, SH, and $NH_2$;

the stereochemistry at positions 3, 5, and 6 is either 3α, 5β, 6β or 3β, 5α, 6α;

each of $R_7$, $R_8$, $R_{15}$, $R_{16}$, $R_{22}$, $R_{24}$, and $R_{25}$ is, independently, selected from H, OH, SH, and $NH_2$;

to a patient with said cancer.

2. The method of claim 1, wherein each of $R_3$, $R_5$, and $R_6$ is OH.

3. The method of claim 2, wherein the stereochemistry at positions 3, 5, and 6 is 3β, 5α, 6α.

4. The method of claim 3, wherein said compound is described by the formula:

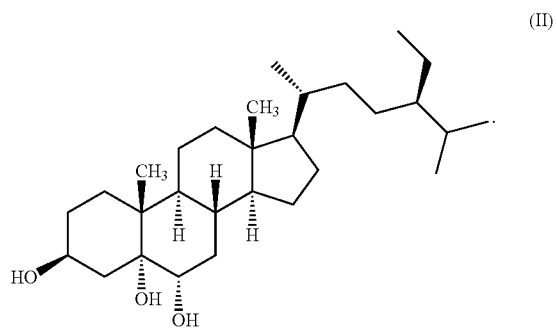

(II)

5. The method of claim 1, wherein said compound is admixed with a pharmaceutically acceptable carrier to form a therapeutic composition.

6. The method of claim 5, wherein said composition is suitable for oral administration.

7. The method of claim 6, wherein said composition is in unit dosage form.

8. The method of claim 7, wherein said compound is present in said unit dosage form in an amount between 0.005 mg and 500 mg.

9. The method of claim 5, wherein said composition is suitable for intrathecal, intraarticular, intratumoral, intravenous, topical, subcutaneous, buccal, intramuscular, inhalation, or rectal administration.

10. The method of claim 4, wherein said cancer is a lymphoma.

11. The method of claim 10, wherein said lymphoma is large B-cell lymphoma.

12. The method of claim 4, wherein said cancer is squamous-cell lung carcinoma.

13. The method of claim 4, wherein said cancer is breast carcinoma.

14. The method of claim 4, wherein said cancer is adenocarcinoma of the lung.

15. The method of claim 4, wherein said cancer is renal cell carcinoma.

16. The method of claim 4, wherein said cancer is prostate cancer.

17. The method of claim 4, wherein said cancer is uterine cancer.

18. The method of claim 4, wherein said cancer is pancreatic cancer.

19. The method of claim 4, wherein said cancer is non-small cell lung cancer.

20. The method of claim 10, wherein said compound is described by the formula:

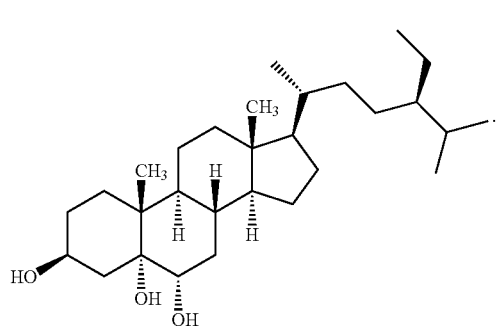

(II)

21. The method of claim 11, wherein said compound is described by the formula:

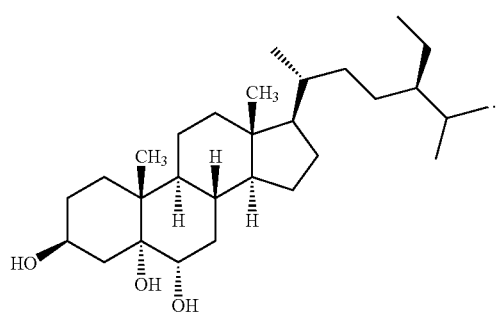

(II)

22. The method of claim 12, wherein said compound is described by the formula:

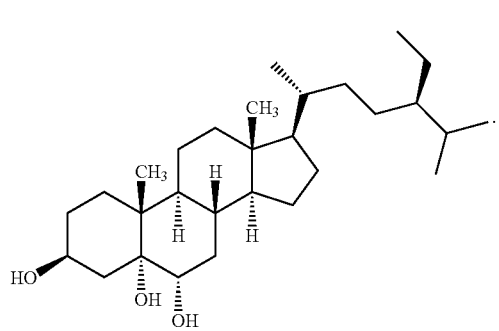

(II)

23. The method of claim 13, wherein said compound is described by the formula:

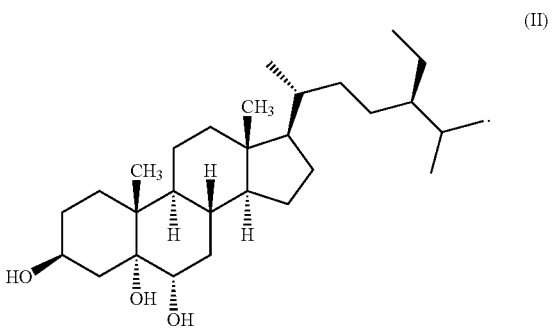

(II)

24. The method of claim 14, wherein said compound is described by the formula:

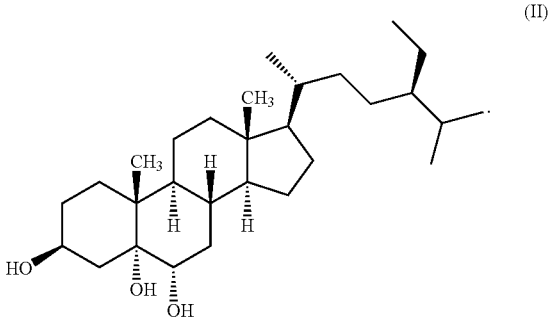

(II)

25. The method of claim 15, wherein said compound is described by the formula:

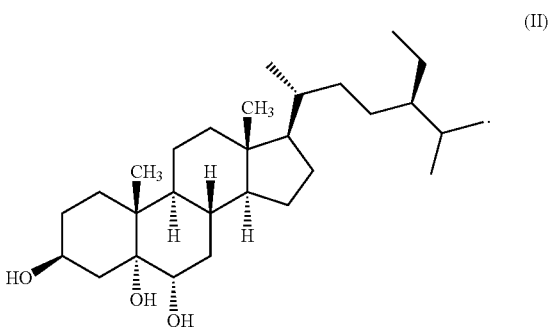

(II)

26. The method of claim 16, wherein said compound is described by the formula:
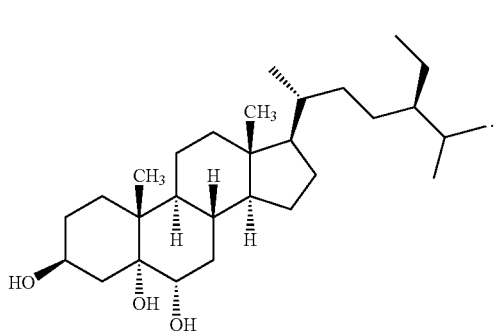
(II)
27. The method of claim 17, wherein said compound is described by the formula:
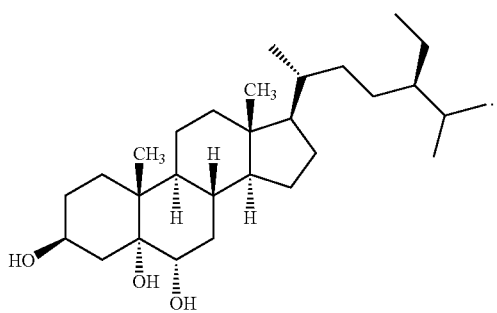
(II)
28. The method of claim 18, wherein said compound is described by the formula:
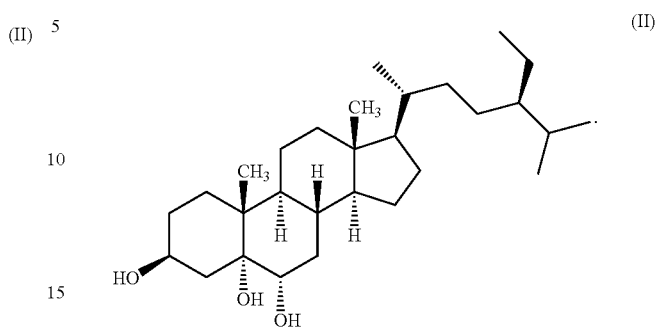
(II)
29. The method of claim 19, wherein said compound is described by the formula:
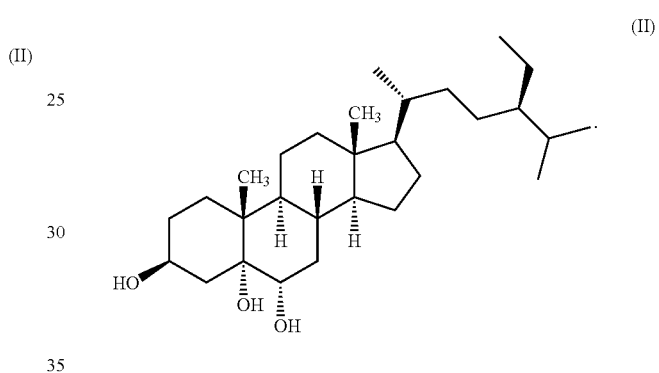
(II)
* * * * *